(12) United States Patent
Armer et al.

(10) Patent No.: US 8,168,673 B2
(45) Date of Patent: May 1, 2012

(54) COMPOUNDS HAVING CRTH2 ANTAGONIST ACTIVITY

(75) Inventors: Richard Edward Armer, Oxon (GB); Carole Eliane Andree Maillol, Oxon (GB); Colin Richard Dorgan, Oxon (GB); Graham Michael Wynne, Oxon (GB); Julia Vile, Oxon (GB)

(73) Assignee: Oxagen Limited, Oxon (GB)

( * ) Notice: Subject to any disclaimer, the term of this patent is extended or adjusted under 35 U.S.C. 154(b) by 287 days.

(21) Appl. No.: 12/357,821

(22) Filed: Jan. 22, 2009

(65) Prior Publication Data

US 2009/0192195 A1     Jul. 30, 2009

(30) Foreign Application Priority Data

Jan. 22, 2008 (GB) .................................. 0801131.4
Jan. 30, 2008 (GB) .................................. 0801672.7

(51) Int. Cl.
*A61K 31/404* (2006.01)
*C07D 209/10* (2006.01)

(52) U.S. Cl. ....................................... 514/415; 548/510

(58) Field of Classification Search ................. 548/510; 514/415
See application file for complete search history.

(56) References Cited

U.S. PATENT DOCUMENTS

| | | | |
|---|---|---|---|
| 3,489,767 A | 1/1970 | Yamamato et al. | |
| 3,557,142 A | 1/1971 | Bell | |
| 4,273,782 A | 6/1981 | Cross et al. | |
| 4,363,912 A | 12/1982 | Cross et al. | |
| 4,859,692 A | 8/1989 | Bernstein et al. | |
| 4,966,911 A | 10/1990 | Clark et al. | |
| 5,641,800 A | 6/1997 | Bach et al. | |
| 6,214,991 B1 | 4/2001 | Jones et al. | |
| 7,582,672 B2 | 9/2009 | Middlemiss et al. | |
| 7,750,027 B2 | 7/2010 | Armer et al. | |
| 2002/0022218 A1 | 2/2002 | Li et al. | |
| 2003/0153751 A1 | 8/2003 | Seehra et al. | |
| 2004/0116488 A1 | 6/2004 | Jennings et al. | |
| 2005/0119268 A1 | 6/2005 | Middlemiss et al. | |
| 2005/0171143 A1 | 8/2005 | Tanimoto et al. | |
| 2007/0232681 A1 | 10/2007 | Middlemiss et al. | |
| 2009/0018138 A1 | 1/2009 | Middlemiss et al. | |
| 2009/0018139 A1 | 1/2009 | Middlemiss et al. | |
| 2009/0018338 A1 | 1/2009 | Middlemiss et al. | |
| 2009/0023788 A1 | 1/2009 | Middlemiss et al. | |
| 2009/0030014 A1 | 1/2009 | Kugimiya et al. | |
| 2009/0186923 A1 | 7/2009 | Armer et al. | |
| 2009/0192195 A1 | 7/2009 | Armer et al. | |
| 2010/0022613 A1 | 1/2010 | Armer et al. | |
| 2010/0041699 A1 | 2/2010 | Boyd et al. | |
| 2010/0266535 A1 | 10/2010 | Armer et al. | |
| 2010/0330077 A1 | 12/2010 | Armer et al. | |
| 2011/0123547 A1 | 5/2011 | Armer et al. | |
| 2011/0124683 A1 | 5/2011 | Hunter et al. | |
| 2011/0142855 A1 | 6/2011 | Armer et al. | |

FOREIGN PATENT DOCUMENTS

| | | |
|---|---|---|
| EP | 0 054 417 A1 | 6/1982 |
| EP | 0 539 117 A1 | 4/1993 |
| EP | 0 851 030 A1 | 7/1998 |
| EP | 1 170 594 A2 | 1/2002 |
| EP | 1 211 513 A1 | 6/2002 |
| EP | 1 505 061 A1 | 2/2005 |
| GB | 1 206 915 | 9/1970 |
| GB | 1 356 834 | 6/1974 |
| GB | 1 407 658 | 9/1975 |
| GB | 1 460 348 | 1/1977 |
| JP | 43024418 | 4/1966 |
| JP | 2001-247570 A | 9/2001 |
| PL | 65781 | 10/1972 |
| WO | WO 9603376 A1 | 2/1996 |
| WO | WO 99/43651 A2 | 9/1999 |
| WO | WO 99/50268 A2 | 10/1999 |

(Continued)

OTHER PUBLICATIONS

Grant & Hackh's Chemical Dictionary (5th Ed. 1987), 147-8 & 542.*

(Continued)

*Primary Examiner* — Jason M Nolan
(74) *Attorney, Agent, or Firm* — Sterne, Kessler, Goldstein & Fox P.L.L.C.

(57) ABSTRACT

Compounds of general formula (I)

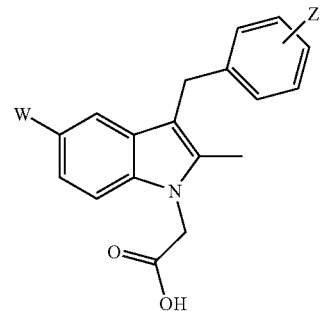

(I)

wherein
W is chloro or fluoro;
Z is a group $SO_2R^1$;
wherein $R^1$ is $—C_3$-$C_8$ cycloalkyl or heterocyclyl optionally substituted with one or more substituents chosen from halo, $—CN$, $—C_1$-$C_6$ alkyl, $—SOR^3$, $—SO_2R^3$, $—SO_2N(R^2)_2$, $—N(R^2)_2$, $—NR^2C(O)R^3$, $—CO_2R^2$, $—CONR^2R^3$, $—NO_2$, $—OR^2$, $—SR^2$, $—O(CH_2)_pOR^2$, and $—O(CH_2)_pO(CH_2)_qOR^2$ wherein
each $R^2$ is independently hydrogen, $—C_1$-$C_6$ alkyl, $—C_3$-$C_8$ cycloalkyl, aryl or heteroaryl;
each $R^3$ is independently, $—C_1$-$C_6$ alkyl, $—C_3$-$C_8$ cycloalkyl, aryl or heteroaryl;
p and q are each independently an integer from 1 to 3;
and their pharmaceutically acceptable salts, hydrates, solvates, complexes or prodrugs are useful in orally administrable compositions for the treatment of allergic diseases such as asthma, allergic rhinitis and atopic dermatitis.

22 Claims, No Drawings

FOREIGN PATENT DOCUMENTS

| | | |
|---|---|---|
| WO | WO 00/32180 A2 | 6/2000 |
| WO | WO 01/51489 A2 | 7/2001 |
| WO | WO 01/64205 A2 | 9/2001 |
| WO | WO 03/066046 A1 | 8/2003 |
| WO | WO 03/066047 A1 | 8/2003 |
| WO | WO 03/097042 A1 | 11/2003 |
| WO | WO 03/097598 A1 | 11/2003 |
| WO | WO 03/101961 A1 | 12/2003 |
| WO | WO 03/101981 A1 | 12/2003 |
| WO | WO 2004/007451 A1 | 1/2004 |
| WO | WO 2004/058164 A2 | 7/2004 |
| WO | WO 2005/019171 A1 | 3/2005 |
| WO | WO 2005/044260 A1 | 5/2005 |
| WO | WO 2005/054232 A1 | 6/2005 |
| WO | WO 2005/094816 A1 | 10/2005 |
| WO | WO 2005/102338 A1 | 11/2005 |
| WO | WO 2006/034419 A2 | 3/2006 |
| WO | WO 2006/092579 A1 | 9/2006 |
| WO | WO 2006/095183 A1 | 9/2006 |
| WO | WO 2007/010964 A1 | 1/2007 |
| WO | WO 2007/031747 A1 | 3/2007 |
| WO | WO 2008/012511 A1 | 1/2008 |
| WO | WO 2009/044134 A1 | 4/2009 |
| WO | WO 2009/044147 A1 | 4/2009 |
| WO | WO 2009/077728 A1 | 6/2009 |

OTHER PUBLICATIONS

Byrn et al., Chapter 11 Hydrates and Solvates in Solid-State Chemistry of Drugs (2nd Ed. 1999), 233-247.*
Morissette et al. Adv. Drug Delivery Rev. 2004, 56, 275-300.*
A.M. Rouhi, Chem. & Eng. News, Feb. 24, 2003, 81(8), 32-35.*
Schafer et al. Drug Discovery Today 2008, 13 (21/22), 913-916.*
Medicines in Development for Mental Illnesses 2010.*
Horig et al., Journal of Translational Medicine 2004, 2(44).*
Pettipher et al., Nature Reviews Drug Discovery 2007, 6, 313-325.*
U.S. Appl. No. 12/293,504, Lovell.
U.S. Appl. No. 11/817,399, Boyd et al.
U.S. Appl. No. 11/908,401, Armer et al.
U.S. Appl. No. 12/374,702, Armer et al.
U.S. Appl. No. 12/357,792, Armer et al.
Cross, P.E. et al., "Selective Thromboxane Synthetase Inhibitors, 2. 3-(1$H$-Imidazol-1-ylmethyl)-2-methyl-1$H$-indole-1-propanoic Acid and Analogues," *J. Med. Chem.* 29:342-346, American Chemical Society, Washington, DC (1986).
Emery, D.L. et al., "Prostaglandin $D_2$ causes accumulation of eosinophils in the lumen of the dog trachea," *J. Appl. Physiol.* 67:959-962, The American Physiological Society, Bethesda, MD (1989).
Fujitani, Y. et al., "Pronounced Eosinophilic Lung Inflammation and Th2 Cytokine Release in Human Lipocalin-Type Prostaglandin D Synthase Transgenic Mice," *J. Immunol.* 168:443-449, The American Association of Immunologists, Bethesda, Maryland (2002).
Gervais, F.G. et al., "Selective modulation of chemokinesis, degranulation, and apoptosis in eosinophils through the $PGD_2$ receptors CRTH2 and DP," *The J. Allergy Clin. Immunol.* 108:982-988, Mosby, St Louis, MO (2001).
Hardy, C. C. et al., "The Bronchoconstrictor Effect of Inhaled Prostaglandin $D_2$ in Normal and Asthmatic Men," *N. Engl. J. Med.* 311:209-213, The Massachusetts Medical Society, Boston, MA (1984).
Hirai, H. et al., "Prostaglandin D2 Selectively Induces Chemotaxis in T Helper Type 2 Cells, Eosinophils, and Basophils via Seven-Transmembrane Receptor CRTH2," *J. Exp. Med.* 193:255-261, The Rockefeller University Press, New York, NY (2001).
Matassa, V. G. et al., "Evolution of a Series of Peptidoleukotriene Antagonists: Synthesis and Structure/Activity Relationships of 1,3,5-Substituted Indoles and Indazoles," *J. Med. Chem.* 33:1781-1790, American Chemical Society, Washington, DC (1990).
Monneret, G. et al., "15R-Methyl-Prostaglandin D2 is a Potent and Selective CRTH2/DP2 Receptor Agonist in Human Eosinophils," *J. Pharmacol. Exp. Ther.* 304:349-355, The American Society of Pharmacology and Experimental Therapeutics, Bethesda, MD (Jan. 2003).
Murray, J. J. et al., "Release of Prostaglandin $D_2$ into Human Airways During Acute Antigen Challenge," *N. Engl. J. Med.* 315:800-804, The Massachusetts Medical Society, Boston, MA (1986).
Paulekuhn, et al., "Trends in Active Pharmaceutical Ingredient Salt Selection Based on Analysis of the Orange Book Database," *Journal of Medicinal Chemistry* 50:6665-6672, The American Chemical Society, Washington, DC (2007).
Sampson, S.E. et al., "Effect of Inhaled Prostaglandin $D_2$ in Normal and Atopic Subjects, and of Pretreatment with Leukotriene $D_4$," *Thorax* 52:513-518, BMJ Publishing Group, London (1997).
Dialog File 351, Accession No. 161699, Derwent WPI English language abstract for JP 43-24418, Apr. 1, 1966.
Patent Abstracts of Japan, English language abstract of JP 2001-247570, Sep. 11, 2001.
International Search Report and Written Opinion of the International Searching Authority for International Application No. PCT/GB2009/000175, mailed Apr. 24, 2009, European Patent Office, Rijswijk, The Netherlands.

* cited by examiner

COMPOUNDS HAVING CRTH2 ANTAGONIST ACTIVITY

The present invention relates to compounds which are useful as pharmaceuticals, to methods for preparing these compounds, compositions containing them and their use in the treatment and prevention of allergic diseases such as asthma, allergic rhinitis and atopic dermatitis and other inflammatory diseases mediated by prostaglandin $D_2$ ($PGD_2$) or other agonists acting at the CRTH2 receptor on cells including eosinophils, basophils and Th2 lymphocytes.

$PGD_2$ is an eicosanoid, a class of chemical mediator synthesised by cells in response to local tissue damage, normal stimuli or hormonal stimuli or via cellular activation pathways. Eicosanoids bind to specific cell surface receptors on a wide variety of tissues throughout the body and mediate various effects in these tissues. $PGD_2$ is known to be produced by mast cells, macrophages and Th2 lymphocytes and has been detected in high concentrations in the airways of asthmatic patients challenged with antigen (Murray et al., (1986), *N. Engl. J. Med.* 315: 800-804). Instillation of $PGD_2$ into airways can provoke many features of the asthmatic response including bronchoconstriction (Hardy et al., (1984) *N. Engl. J. Med.* 311: 209-213; Sampson et al., (1997) *Thorax* 52: 513-518) and eosinophil accumulation (Emery et al., (1989) *J. Appl. Physiol.* 67: 959-962).

The potential of exogenously applied $PGD_2$ to induce inflammatory responses has been confirmed by the use of transgenic mice overexpressing human $PGD_2$ synthase which exhibit exaggerated eosinophilic lung inflammation and Th2 cytokine production in response to antigen (Fujitani et al., (2002) *J. Immunol.* 168: 443-449).

The first receptor specific for $PGD_2$ to be discovered was the DP receptor which is linked to elevation of the intracellular levels of cAMP. However, $PGD_2$ is thought to mediate much of its proinflammatory activity through interaction with a G protein-coupled receptor termed CRTH2 (chemoattractant receptor-homologous molecule expressed on Th2 cells) which is expressed by Th2 lymphocytes, eosinophils and basophils (Hirai et al., (2001) *J. Exp. Med.* 193: 255-261, and EP0851030 and EP-A-1211513 and Bauer et al., EP-A-1170594). It seems clear that the effect of $PGD_2$ on the activation of Th2 lymphocytes and eosinophils is mediated through CRTH2 since the selective CRTH2 agonists 13,14 dihydro-15-keto-$PGD_2$ (DK-$PGD_2$) and 15R-methyl-$PGD_2$ can elicit this response and the effects of $PGD_2$ are blocked by an anti-CRTH2 antibody (Hirai et al., 2001; Monneret et al., (2003) *J. Pharmacol. Exp. Ther.* 304: 349-355). In contrast, the selective DP agonist BW245C does not promote migration of Th2 lymphocytes or eosinophils (Hirai et al., 2001; Gervais et al., (2001) *J. Allergy Clin. Immunol.* 108: 982-988). Based on this evidence, antagonising $PGD_2$ at the CRTH2 receptor is an attractive approach to treat the inflammatory component of Th2-dependent allergic diseases such as asthma, allergic rhinitis and atopic dermatitis.

EP-A-1170594 suggests that the method to which it relates can be used to identify compounds which are of use in the treatment of allergic asthma, atopic dermatitis, allergic rhinitis, autoimmune, reperfusion injury and a number of inflammatory conditions, all of which are mediated by the action of $PGD_2$ or other agonists at the CRTH2 receptor.

Compounds which bind to CRTH2 are taught in WO-A-03066046 and WO-A-03066047. These compounds are not new but were first disclosed, along with similar compounds, in GB 1356834, GB 1407658 and GB 1460348, where they were said to have anti-inflammatory, analgesic and antipyretic activity. WO-A-03066046 and WO-A-03066047 teach that the compounds to which they relate are modulators of CRTH2 receptor activity and are therefore of use in the treatment or prevention of obstructive airway diseases such as asthma, chronic obstructive pulmonary disease (COPD) and a number of other diseases including various conditions of bones and joints, skin and eyes, GI tract, central and peripheral nervous system and other tissues as well as allograft rejection. These compounds are all indole derivatives with an acetic acid substituent at the 3-position of the indole ring.

PL 65781 and JP 43-24418 also relate to indole-3 acetic acid derivatives which are similar in structure to indomethacin and, like indomethacin, are said to have anti-inflammatory and antipyretic activity. Thus, although this may not have been appreciated at the time when these documents were published, the compounds they describe are COX inhibitors, an activity which is quite different from that of the compounds of the present invention. Indeed, COX inhibitors are contraindicated in the treatment of many of the diseases and conditions, for example asthma and inflammatory bowel disease for which the compounds of the present invention are useful, although they may sometimes be used to treat arthritic conditions.

There is further prior art which relates to indole-1-acetic acid compounds, although these are not described as CRTH2 antagonists. For example WO-A-9950268, WO-A-0032180, WO-A-0151849 and WO-A-0164205 all relate to compounds which are indole-1-acetic acid derivatives but these compounds are said to be aldose reductase inhibitors useful in the treatment of diabetes mellitus (WO-A-9950268, WO-A-0032180 and WO-A-0164205) or hypouricemic agents (WO-A-0151849). There is no suggestion in any of these documents that the compounds would be useful for the treatment of diseases and conditions mediated by $PGD_2$ or other CRTH2 receptor agonists.

U.S. Pat. No. 4,363,912 relates to indole-1-acetic acid derivatives which are said to be inhibitors of thromboxane synthetase and to be useful in the treatment of conditions such as thrombosis, ischaemic heart disease and stroke.

WO-A-9603376 relates to compounds which are said to be $sPLA_2$ inhibitors which are useful in the treatment of bronchial asthma and allergic rhinitis. These compounds all have amide or hydrazide substituents in place of the carboxylic acid derivative of the compounds of the present invention.

JP 2001247570 relates to a method of producing a 3-benzothiazolylmethyl indole acetic acid, which is said to be an aldose reductase inhibitor.

U.S. Pat. No. 4,859,692 relates to compounds which are said to be leukotriene antagonists useful in the treatment of conditions such as asthma, hay fever and allergic rhinitis as well as certain inflammatory conditions such as bronchitis, atopic and ectopic eczema. Some of the compounds of this document are indole-1-acetic acids but the same authors, in *J. Med. Chem.*, 33, 1781-1790 (1990), teach that compounds with an acetic acid group on the indole nitrogen do not have significant peptidoleukotriene activity.

U.S. Pat. No. 4,273,782 is directed to indole-1-acetic acid derivatives which are said to be useful in the treatment of conditions such as thrombosis, ischaemic heart disease, stroke, transient ischaemic attack, migraine and the vascular complications of diabetes. There is no mention in the document of conditions mediated by the action of $PGD_2$ or other agonists at the CRTH2 receptor.

U.S. Pat. No. 3,557,142 relates to 3-substituted-1-indole carboxylic acids and esters which are said to be useful in the treatment of inflammatory conditions.

WO-A-03/097598 relates to compounds which are CRTH2 receptor antagonists. They do not have an aryl substituent at the indole-3 position.

Cross et al., *J. Med. Chem.* 29, 342-346 (1986) relates to a process for preparing indole-1-acetic acid derivatives from the corresponding esters. The compounds to which it relates are said to be inhibitors of thromboxane synthetase.

EP-A-0539117 relates to indole-1-acetic acid derivatives which are leukotriene antagonists.

US 2003/0153751 relates to indole-1-acetic acid derivatives which are sPLA$_2$ inhibitors. However, all of the exemplified compounds have bulky substituents at the 2- and 5-positions of the indole system and are therefore very different from the compounds of the present invention.

US 2004/011648 discloses indole-1-acetic acid derivatives which are inhibitors of PAI-1. There is no suggestion that the compounds might have CRTH2 antagonist activity.

WO 2004/058164 relates to compounds which are said to be asthma and allergic inflammation modulators. The only compounds for which activity is demonstrated are entirely different in structure from the indole-1-acetic acid derivatives of the present invention.

Compounds which bind to the CRTH2 receptor are disclosed in WO-A-03/097042 and WO-A-03/097598. These compounds are indole acetic acids but in WO-A-03/097042 the indole system is fused at the 2-3 positions to a 5-7 membered carbocyclic ring. In WO-A-03/097598 there is a pyrrolidine group at the indole 3-position.

WO-A-03/101981, WO-A-03/101961 and WO-A-2004/007451 all relate to indole-1-acetic acid derivatives which are said to be CRTH2 antagonists but which differ in structure from the compounds of general formula (I) because there is no spacer or an —S— or —SO$_2$— group attached to the indole 3-position in place of the CH$_2$ group of the compounds of the present invention as described below.

WO-A-2005/019171 also describes indole-1-acetic acid derivatives which are said to be CRTH2 antagonists and which are said to be useful for the treatment of various respiratory diseases. These compounds all have a substituent which is linked to the indole-3 position by an oxygen spacer.

WO-A-2005/094816 again describes indole-1-acetic acid compounds, this time with an aliphatic substituent at the 3-position of the indole ring. The compounds are said to be CRTH2 antagonists.

WO-A-2006/034419 relates to CRTH2 antagonist indole compounds which have a heterocyclic or heteroaryl substituent directly linked to the 3-position of the indole ring system.

In our earlier application, WO-A-2005/044260, we describe compounds which are antagonists of PGD$_2$ at the CRTH2 receptor. These compounds are indole-1-acetic acid derivatives substituted at the 3-position with a group CR$^8$R$^9$, wherein R$^9$ is hydrogen or alkyl and R$^8$ is an aryl moiety which may be substituted with one or more substituents. The compounds described in this document are potent antagonists in vitro of PGD$_2$ at the CRTH2 receptor. However, we have found that when tested in vivo, the pharmacokinetic profile of some compounds is not optimal and their potency in the whole blood eosinophil shape change test, which gives an indication of the likely in vivo activity of the compounds, is often somewhat less than might have been expected from the in vitro binding results.

In another of our earlier applications, WO2006/095183, the indole-1-acetic acid derivatives are substituted at the 3-position with a 1-benzenesulfonyl-1H-pyrrol-2-ylmethyl group, where the phenyl group of the benzenesulfonyl moiety may be substituted. These compounds are extremely active CRTH2 antagonists but are rapidly metabolised as determined by incubation with human microsome preparations.

Our application WO2008/012511 also relates to CRTH2 antagonist compounds, this time to indole-1-acetic acid derivatives substituted at the 3-position with a 2-phenylsulfonylbenzyl group. It was found that the position of the phenylsulfonyl substituent had a significant effect on both the activity of the compounds and their pharmacokinetic profile.

The present invention relate to analogues of the compounds of WO2008/012511 in which the 2-phenylsulfonylbenzyl group is replaced by a heterocyclylsulfonylbenzyl group.

In the present invention there is provided a compound of general formula (I)

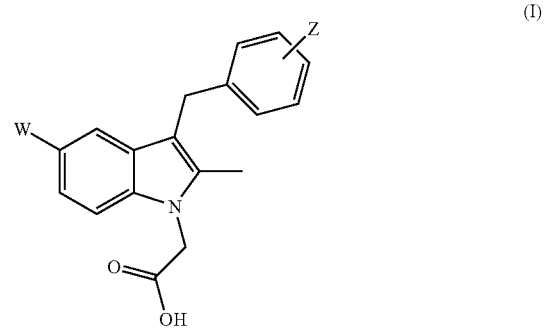

(I)

wherein
W is chloro or fluoro;
Z is a group SO$_2$R$^1$;
wherein R$^1$ is —C$_3$-C$_8$ cycloalkyl or heterocyclyl either of which is optionally substituted with one or more substituents chosen from halo, —CN, —C$_1$-C$_6$ alkyl, —SOR$^3$, —SO$_2$R$^3$, —SO$_2$N(R$^2$)$_2$, —N(R$^2$)$_2$, —NR$^2$C(O)R$^3$, —CO$_2$R$^2$, —CONR$^2$R$^3$, —NO$_2$, —OR$^2$, —SR$^2$, —O(CH$_2$)$_p$OR$^2$, and —O(CH$_2$)$_p$O(CH$_2$)$_q$OR$^2$ wherein
each R$^2$ is independently hydrogen, —C$_1$-C$_6$ alkyl, —C$_3$-C$_8$ cycloalkyl, aryl or heteroaryl;
each R$^3$ is independently, —C$_1$-C$_6$ alkyl, —C$_3$-C$_8$ cycloalkyl, aryl or heteroaryl;
p and q are each independently an integer from 1 to 3;
or a pharmaceutically acceptable salt, hydrate, solvate, complex or prodrug thereof.

The compounds of general formula (I) are antagonists at the CRTH2 receptor and are useful in the treatment of diseases and conditions which are mediated by PGD$_2$ or other agonists binding to the CRTH2 receptor. These include allergic diseases, asthmatic conditions and inflammatory diseases, examples of which are asthma, including allergic asthma, bronchial asthma, exacerbations of asthma and related allergic diseases caused by viral infection, particularly those exacerbations caused by rhinovirus and respiratory syncytial virus intrinsic, extrinsic, exercise-induced, drug-induced and dust-induced asthma, treatment of cough, including chronic cough associated with inflammatory and secretory conditions of the airways and iatrogenic cough, acute and chronic rhinitis, including rhinitis medicamentosa, vasomotor rhinitis, perennial allergic rhinitis, seasonal allergic rhinitis, nasal polyposis, acute viral infection including common cold, infection due to respiratory syncytial virus, influenza, coronavirus and adenovirus, atopic dermatitis, contact hypersensitivity (including contact dermatitis), eczematous dermatitis, phyto dermatitis, photo dermatitis, sebhorroeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa urticaria, angioedema, vasculitides, toxic erythemas, cutaneous eosinophilias, alopecia areata, male-pattern baldness, Sweet's syndrome, Weber-Christian syndrome, erythema multiforme, cellulitis, panniculitis, cutaneous lymphomas, non-melanoma skin cancer and other dysplastic lesions; blepharitis conjunctivitis, especially allergic conjunctivitis, anterior and posterior uveitis, chorioditis, autoimmune, degenerative or inflammatory disorders affecting the retina, ophthalmitis; bronchitis, including infectious and eosinophilic bronchitis, emphysema, bronchiectasis, farmer's lung, hypersensitivity pneumonitis, idiopathic interstitial pneumonias, complications of lung transplantation, vasculitic and thrombotic disorders of the lung vasculature, pulmonary hypertension, food allergies, gingivitis, glossitis, periodontitis, oesophagitis including reflux, eosinophilic gastroenteritis, proctitis, pruris ani, celiac disease, food-related allergies, inflammatory bowel disease, ulcerative colitis and Crohn's disease, mastocytosis and also other CRTH2-mediated diseases, for example autoimmune diseases such as hyper IgE syndrome, Hashimoto's thyroiditis, Graves' disease, Addison's disease, diabetes mellitus, idiopathic thrombocytopaenic purpura, eosinophilic paschiitis, antiphospholipid syndrome and systemic lupus erythematosus, AIDS, leprosy, Sezary syndrome, paraneoplastic syndrome, mixed and undifferentiated connective tissue diseases, inflammatory myopathies including dermatomyositis and polymyositis, polymalgia rheumatica, juvenile arthritis, rheumatic fever, vasculitides including giant cell arteritis, Takayasu's arteritis, Churg-Strauss syndrome, polyarteritis nodosa, microscopic polyarteritis, temporal arteritis, myasthenia gravis, acute and chronic pain, neuropathic pain syndromes, central and peripheral nervous system complications of malignant, infectious or autoimmune processes, low back pain, familial Mediterranean Fever, Muckle-Wells syndrome, Familial Hibernian fever, Kikuchi disease, psoriasis, acne, multiple sclerosis, allograft rejection, reperfusion injury, chronic obstructive pulmonary disease, as well as rheumatoid arthritis, Still's disease, ankylosing spondylitis, reactive arthritis, undifferentiated spondarthropathy, psoriatic arthritis, septic arthritis and other infection-related arthopathies and bone disorders and osteoarthritis; acute and chronic crystal-induced synovitis including urate gout, calcium pyrophosphate deposition disease, calcium paptite related tendon syndrome and synovial inflammation, Behcet's disease, primary and secondary Sjogren's syndrome systemic sclerosis and limited scleroderma; hepatitis, cirrhosis of the liver, cholecystitis, pancreatitis, nephritis, nephritic syndrome, cystitis and Hunner's ulcer, acute and chronic urethritis, prostatitis, epididymitis, oophoritis, salpingitis, vulvo-vaginitis, Peyronie's disease, erectile dysfunction, Alzheimer's disease and other dementing disorders; pericarditis, myocarditis, inflammatory and auto-immune cardiomyopathies including myocardial sarcoid, ischaemic reperfusion injuries, endocarditis, valvulitis, aortitis, phlebitis, thrombosis, treatment of common cancers and fibrotic conditions such as idiopathic pulmonary fibrosis including cryptogenic fibrosing alveolitis, keloids, excessive fibrotic scarring/adhesions post surgery, liver fibrosis including that associated with hepatitis B and C, uterine fibroids, sarcoidosis, including neurosarcoidosis, scleroderma, kidney fibrosis resulting from diabetes, fibrosis associated with RA, atherosclerosis, including cerebral atherosclerosis, vasculitis, myocardial fibrosis resulting from myocardial infarction, cystic fibrosis, restenosis, systemic sclerosis, Dupuytren's disease, fibrosis complicating anti-neoplastic therapy and chronic infection including tuberculosis and aspergillosis and other fungal infections, CNS fibrosis following stroke or the promotion of healing without fibrotic scarring.

The compounds are particularly effective when used for the treatment of allergic asthma, perennial allergic rhinitis, seasonal allergic rhinitis, atopic dermatitis, contact hypersensitivity (including contact dermatitis), conjunctivitis, especially allergic conjunctivitis, vernal keratoconjunctivitis and atopic keratoconjunctivitis, eosinophilic bronchitis, food allergies, eosinophilic gastroenteritis, inflammatory bowel disease, ulcerative colitis and Crohn's disease, mastocytosis and also other PGD2-mediated diseases, for example autoimmune diseases such as hyper IgE syndrome and systemic lupus erythematus, psoriasis, acne, multiple sclerosis, allograft rejection, reperfusion injury, chronic obstructive pulmonary disease, as well as rheumatoid arthritis, psoriatic arthritis, osteoarthritis and fibrotic diseases caused/exacerbated by Th2 immune responses, for example idiopathic pulmonary fibrosis and hypertrophic scars.

In the present specification "$C_1$-$C_6$ alkyl" refers to a straight or branched saturated hydrocarbon chain having one to six carbon atoms and optionally substituted with one or more halo substituents and/or with one or more $C_3$-$C_8$ cycloalkyl groups. Examples include methyl, ethyl, n-propyl, isopropyl, t-butyl, n-hexyl, trifluoromethyl, 2-chloroethyl, methylenecyclopropyl, methylenecyclobutyl, methylenecyclobutyl and methylenecyclopentyl.

The term "$C_1$-$C_{18}$ alkyl" has a similar meaning to the above except that it refers to a straight or branched saturated hydrocarbon chain having one to eighteen carbon atoms.

In the present specification "$C_3$-$C_8$ cycloalkyl" refers to a saturated carbocyclic group having three to eight ring atoms and optionally substituted with one or more halo substituents. Examples include cyclopropyl, cyclopentyl, cyclohexyl and fluorocyclohexyl.

The term "heterocyclyl" in the context of the specification refers to a saturated ring system having from 4 to 8 ring atoms, at least one of which is a heteroatom selected from N, O and S, and which is optionally substituted by one or more substituents chosen from halo and oxo. Examples of heterocyclyl groups include azetidinyl, piperidinyl; tetrahydrofuranyl, tetrahydropyranyl, dioxanyl, thiomorpholinyl, 1,1-dioxo-thiomorpholinyl, morpholinyl, pyrrolidinyl, 4,4-difluoropiperidinyl, piperizinyl, azepanyl, 1,4-diazepanyl, 1,4-oxazepanyl and azocanyl.

In the present specification, "halo" refers to fluoro, chloro, bromo or iodo.

The term "aryl" in the context of the present specification refers to a ring system with aromatic character having from 5 to 14 ring carbon atoms and containing up to three rings. Where an aryl moiety contains more than one ring, not all rings must be fully aromatic in character. Examples of aryl moieties are benzene, naphthalene, indane and indene.

The term "heteroaryl" in the context of the specification refers to a ring system with aromatic character having from 5 to 14 ring atoms, at least one of which is a heteroatom selected from N, O and S, and containing up to three rings. Where a heteroaryl moiety contains more than one ring, not all rings must be fully aromatic in character. Examples of heteroaryl groups include pyridine, pyrimidine, indole, benzofuran, benzimidazole and indolene.

General formula (I) as shown above is intended to include all isotopic variants, for example the hydrogen atoms of the molecule can be $^1H$, $^2H$ or $^3H$ and the carbon atoms can be $^{12}C$ or $^{14}C$.

Appropriate pharmaceutically and veterinarily acceptable salts of the compounds of general formulae (I) include basic addition salts such as sodium, potassium, calcium, aluminium, zinc, magnesium and other metal salts as well as choline, diethanolamine, ethanolamine, ethyl diamine, meglumine and other well known basic addition salts as summarised in *J. Med. Chem.*, 50, 6665-6672 (2007) and/or known to those skilled in the art.

Salts which are not pharmaceutically or veterinarily acceptable may still be valuable as intermediates.

Prodrugs are any covalently bonded compounds which release the active parent drug according to general formula (I) in vivo. Examples of prodrugs include alkyl esters of the compounds of general formula (I), for example the esters of general formula (II) below.

In suitable compounds of general formula (I), independently or in combination: W is a fluoro substituent; and $R^1$ is a cycloalkyl group or a nitrogen-containing heterocyclic group, for example a pyrrole, piperidine, cyclobutyl, cyclopentyl or cyclohexyl group, any of which may be substituted as set out above.

When $R^1$ is a nitrogen-containing heterocyclic ring, it is suitably linked to the $SO_2$ group via a ring nitrogen atom.

More suitably, $R^1$ is a 5- or 6-membered ring, and in particular a cyclopentyl, cyclohexyl, pyrrolidinyl or piperidinyl ring. When $R^1$ is pyrrolidinyl or piperidinyl, it may be attached to the $SO_2$ group via the ring nitrogen atom.

Compounds in which $R^1$ is a 6-membered ring appear to be slightly more active than compounds in which $R^1$ is a 5-membered ring.

In addition, the inventors noted that more active compounds are those in which the group Z is at the 2-position of the phenyl ring to which it is attached.

Some of the compounds of the present invention have extremely high intrinsic CRTH2 antagonist activity and this activity is also seen in experiments carried out in whole blood.

Example compounds of the present invention include:
2-(3-(2-(Cyclohexylsulfonyl)benzyl)-5-fluoro-2-methyl-1H-indol-1-yl)acetic acid (Compound 1);
2-(5-Fluoro-2-methyl-3-(2-(piperidin-1-ylsulfonyl)benzyl)-1H-indol-1-yl)acetic acid (Compound 2);
2-(3-(2-(Cyclopentylsulfonyl)benzyl)-5-fluoro-2-methyl-1H-indol-1-yl)acetic acid (Compound 3);
2-(5-Fluoro-2-methyl-3-(3-(piperidin-1-ylsulfonyl)benzyl)-1H-indol-1-yl)acetic acid (Compound 4);
2-(5-Fluoro-2-methyl-3-(2-(pyrrolidin-1-ylsulfonyl)benzyl)-1H-indol-1-yl)acetic acid (Compound 5);
2-(3-(4-(Cyclohexylsulfonyl)benzyl)-5-fluoro-2-methyl-1H-indol-1-yl)acetic acid (Compound 6);
2-(3-(4-(Cyclopentylsulfonyl)benzyl)-5-fluoro-2-methyl-1H-indol-1-yl)acetic acid (Compound 7);
2-(3-(2-(Cyclobutylsulfonyl)benzyl)-5-fluoro-2-methyl-1H-indol-1-yl)acetic acid (Compound 8);
2-(5-Fluoro-2-methyl-3-(3-(pyrrolidin-1-ylsulfonyl)benzyl)-1H-indol-1-yl)acetic acid (Compound 9);
2-(5-Fluoro-2-methyl-3-(4-(piperidin-1-ylsulfonyl)benzyl)-1H-indol-1-yl)acetic acid (Compound 10);
or the $C_1$-$C_6$ alkyl, aryl, $(CH_2)_mOC(=O)C_1$-$C_6$alkyl, $((CH_2)_mO)_nCH_2CH_2X$, $(CH_2)_mN(R^5)_2$ or $CH((CH_2)_mO(C=O)R^6)_2$ ester thereof;
  m is 1 or 2;
  n is 1-4;
  X is $OR^5$ or $N(R^5)_2$;
  $R^5$ is hydrogen or methyl;
  $R^6$ is $C_1$-$C_{18}$ alkyl.

In a further aspect of the present invention, there is provided a compound of general formula (II):

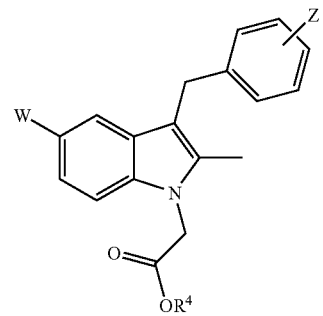

II wherein W and Z are as defined for general formula (I); and $R^4$ is $C_1$-$C_6$ alkyl, $C_1$-$C_6$ alkyl substituted with aryl, aryl, $(CH_2)_mOC(=O)C_1$-$C_6$alkyl, $((CH_2)_mO)_nCH_2CH_2X$, $(CH_2)_mN(R^5)_2$ or $CH((CH_2)_mO(C=O)R^6)_2$;
  m is 1 or 2;
  n is 1-4;
  X is $OR^5$ or $N(R^5)_2$;
  $R^5$ is hydrogen or methyl;
  $R^6$ is $C_1$-$C_{18}$ alkyl
or a pharmaceutically acceptable salt, hydrate, solvate, complex or prodrug thereof.

Compounds of general formula (II) are novel and may be used as prodrugs for compounds of general formula (I). When the compound of general formula (II) acts as a prodrug, it is later transformed to the drug by the action of an esterase in the blood or in a tissue of the patient.

Examples of particularly suitable $R^4$ groups when the compound of general formula (II) is used as a prodrug include: methyl, ethyl, propyl, phenyl, $—O(CH_2)_2O(CH_2)_2OR^5$, $—O(CH_2)_2O(CH_2)_2O(CH_2)_2OR^5$, $—O(CH_2)_2O(CH_2)_2NR^5_2$, $—O(CH_2)_2O(CH_2)_2O(CH_2)_2NR^5_2$, $—CH_2C(=O)$ tBu, $—CH_2CH_2N(Me)_2$, $—CH_2CH_2NH_2$ or $—CH(CH_2O(C=O)R^6)_2$ wherein $R^5$ and $R^6$ are as defined above.

In addition to their use as prodrugs, compounds of formula (II) wherein $R^4$ is $C_1$-$C_6$ alkyl or benzyl may be used in a process for the preparation of a compound of general formula (I), the process comprising reacting the compound of general formula (II) with a base such as sodium hydroxide or lithium hydroxide. The reaction may take place in an aqueous solvent or an organic solvent or a mixture of the two. A typical solvent used for the reaction is a mixture of tetrahydrofuran and water and the reaction is described in detail in Procedure L of the examples below.

Compounds of general formula (II) may be prepared from compounds of general formula (III):

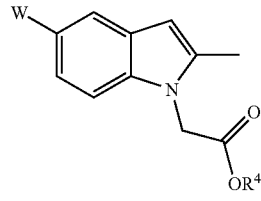

III wherein W and $R^4$ are as defined in general formula (II); by reaction with an aldehyde of general formula (IV):

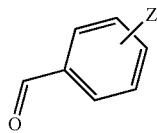
(IV)

wherein Z is $SO_2R^1$ and $R^1$ is as defined for general formula (I). The reaction may be carried out in the presence of trifluoroacetic acid and triethylsilane in a polar organic solvent such as dichloromethane and typically at room temperature (15 to 25° C.). This reaction is described in detail in Procedure K of the Examples below.

Procedures for the preparation of compounds of general formula (III) are known to those skilled in the art and in general involve alkylation of a 5-halo-2-methylindole derivative at the 1-position with an alpha-bromoacetate derivative or related alkylating agent.

Certain compounds of general formula (IV) in which $R^1$ is an optionally substituted cycloalkyl group or a heterocyclic group which is not attached to the $SO_2$ moiety via a nitrogen atom may be prepared by the oxidation of a compound of general formula (V):

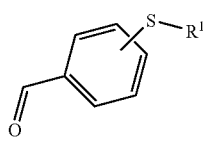
(V)

wherein $R^1$ is an optionally substituted cycloalkyl group or a heterocyclic group as defined for general formula (I) and wherein the heterocyclic group is not attached to the $SO_2$ moiety via a nitrogen atom.

In some cases, the conversion may be achieved by protecting the compound of general formula (V) as an acetal of general formula (VI):

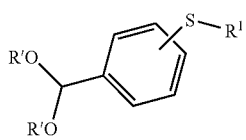
(VI)

wherein $R^1$ is as defined for general formula (I) and R' represents $C_1$-$C_6$ alkyl, phenyl, benzyl or the two R' groups may be linked together to form a cyclic acetal group, e.g. by condensation with a $C_2$-$C_4$ diol such as propylene glycol or ethylene glycol.

Methods for forming acetals and their use as protecting groups are well known in the art and are described, for example in "Protecting Groups in Organic Synthesis", Theodora W. Greene and Peter G. M. Wuts, published by John Wiley & Sons Inc. Typically, however, the acetal of general formula (VI) may be formed by reaction with trimethylorthoformate and p-toluene sulfonic acid followed by NaOR', where R' is as defined above, in the appropriate alcoholic solvent. For example when R' is methyl, the reaction may be carried out using sodium methoxide in methanol. The reaction may initially be conducted in an anhydrous organic solvent such as methanol and under an inert atmosphere, typically nitrogen. The reaction is described in detail in Procedure E set out below.

The compound of general formula (VI) may be oxidised to form a compound of general formula (VII)

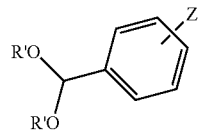
(VII)

where Z is a group $SO_2R^1$ wherein $R^1$ is as defined for general formula (V) and R' groups are as defined for general formula (VI);
by reaction with an oxidising agent such as 3-chloroperoxybenzoic acid (mCPBA) in a polar solvent such as dichloromethane. The reagents may be mixed at reduced temperature, for example −10 to 10° C. and the reaction mixture subsequently allowed to warm, for example to room temperature of about 15 to 25° C. This is described in detail for specific examples in Procedure F of the examples below.

The oxidation step is usually be followed by the deprotection of the compound of general formula (VII) to form a compound of general formula (IV). The deprotection may be carried out by a standard method, for example by treating with aqueous acid, particularly sulfuric acid, followed by neutralisation with a base such as potassium carbonate as described in detail in Procedure G of the examples.

This method of forming the compound of general formula (IV) is particularly useful when the Z substituent is at the 4-position of the phenyl ring.

In some cases, particularly when Z is at the 2- or 3-position of the phenyl ring, protection is not necessary and the compound of general formula (IV) can be prepared directly from the compound of general formula (V) by direct oxidation using mCPBA in dichloromethane as described above. This is illustrated by Procedure B of the examples below.

A compound of general formula (V) may be prepared by reacting a compound of general formula (VIII):

(VIII)

where Hal is fluoro, chloro or bromo;
with a compound of general formula (IX):

HSR$^1$  (IX)

wherein $R^1$ is as defined for general formula (V);
This substitution reaction may be carried out in the presence of a weak base such as potassium carbonate, in an organic solvent such as DMSO and under an inert atmosphere such as nitrogen. The reaction mixture may also be heated, for example at about 80 to 120° C., typically 100° C. An example of this reaction is set out in Procedure A below.

Compounds of general formulae (VIII) and (IX) are readily available or can be prepared by methods well known to those of skill in the art.

Alternatively, a compound of general formula (V) may be prepared from a compound of general formula (X):

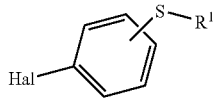
(X)

where Hal is F, Cl or Br and Y and R¹ as defined in general formula (V);
by treatment with n-butyl lithium in THF followed by the addition of DMF. This is illustrated by Procedure D of the examples.

A compound of general formula (X) may be prepared from a compound of general formula (XI):

(XI)

where Hal is as defined above;
by reaction with a compound of general formula (XII):

X—R¹ (XII)

where X is a leaving group, for example toluene sulfonyl or halo and R¹ as defined in general formula (V).

The reaction may be carried out in a polar organic solvent such as acetonitrile and in the presence of a weak base such as caesium carbonate as described in Procedure C of the examples.

Compounds of general formulae (XI) and (XII) are well known and are readily available or can be prepared by methods well known to those of skill in the art. A method for preparing compounds of general formula (XII) in which X is toluene sulfonyl from a compound of formula R¹—OH is described in Procedure Z of the examples.

Compounds of general formula (IV) in which R¹ is a nitrogen containing heterocyclic group which is joined to the SO₂ moiety via the nitrogen atom require a different method of preparation. These compounds may be prepared by reacting a compound of general formula (XVII):

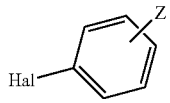
(XVII)

where Hal is F, Cl or Br and Z is an optionally substituted —C₃-C₈ heterocyclyl group as defined in general formula (I);
by treatment with n-butyl lithium in THF followed by the addition of DMF.

Compounds of general formula (IV) in which R¹ is a nitrogen containing heterocyclic group which is joined to the SO₂ moiety via the nitrogen atom may also be prepared from compounds of general formula (XVIII):

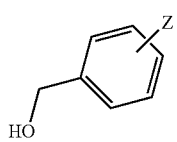
(XVIII)

wherein Z is SO₂R¹ and R¹ is a nitrogen containing heterocyclic group which is joined to the SO₂ moiety via the nitrogen atom;
by reaction with pyridinium chlorochromate (PCC) in a suitable solvent such as acetonitrile as illustrated in Procedure J of the examples.

Compounds of general formula (XVIII) may be prepared from carboxylic acids of general formula (XIX):

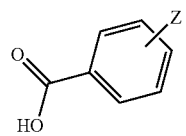
(XIX)

wherein Z is SO₂R¹ and R¹ is a nitrogen containing heterocyclic group which is joined to the SO₂ moiety via the nitrogen atom;
by reaction with a suitable reducing agent for example borane, which may be in the form of borane-tetrahydrofuran complex. An example of this reaction is set out in Procedure I below.

A compound of general formula (XIX) may be prepared from a compound of general formula (XX):

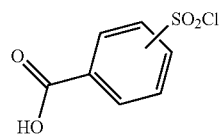
(XX)

by reaction with a heterocyclic amine of general formula (XIV):

R¹—H (XIV)

wherein R¹ is an optionally substituted —C₃-C₈ heterocyclyl as defined in general formula (I) in which the H shown in the formula is linked to a ring nitrogen atom. An example of this reaction is given in Procedure H below.

Compounds of general formulae (XIV) and (XX) are well known to those of skill in the art and are readily available or may be prepared by known methods.

Compounds of general formula (II) in which R¹ is a nitrogen containing heterocyclic group which is joined to the SO₂ moiety via a nitrogen atom may also be prepared by reacting a compound of general formula (XIII):

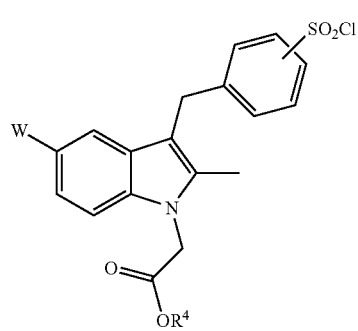
(XIII)

wherein R⁴ is as defined in general formula (II);
with a heterocyclic amine of general formula (XIV) as defined above.

Typically, the reaction is conducted in pyridine and is allowed to proceed at a temperature of from 15 to 25° C., generally room temperature, for up to 20 hours as set out in Procedure Q below.

A compound of general formula (XIII) may be prepared by reacting a compound of general formula (XV):

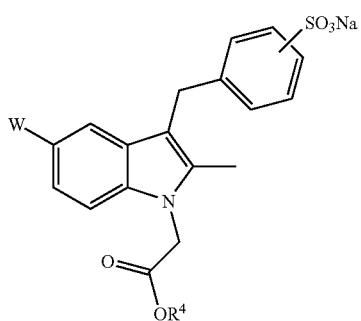

(XV)

wherein W is as defined in general formula (I) and $R^4$ is as defined in general formula (II); with chlorosulfonic acid at a temperature of 15 to 25° C. (typically room temperature) as described in detail in Procedure P of the examples.

Chlorosulfonic acid is a readily available reagent.

A compound of general formula (XV) may be prepared from a compound of general formula (III) as defined above by reaction with a compound of general formula (XVI):

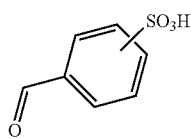

(XVI)

The reaction may be carried out in the presence of trifluoroacetic acid and triethylsilane in a polar organic solvent such as dichloromethane and typically at room temperature (15 to 25° C.). The —SO$_3$H group is subsequently converted to a —SO$_3$Na group. An example of this reaction is given in Procedure N below.

Compounds of formula (XVI) are well known to those of skill in the art and are readily available.

A compound of general formula (XIII) as defined above may also be prepared from a compound of general formula (XVII):

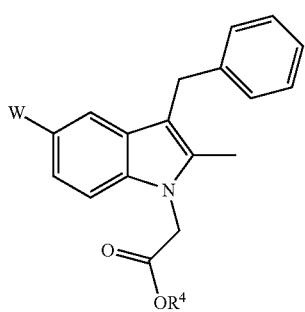

(XVII)

wherein W and $R^4$ are as defined for general formula (I) and general formula (II) respectively;
by reaction with chlorosulfonic acid. The reaction may be initiated at 0° C. and then the mixture subsequently allowed to warm to room temperature (15 to 250). The process is described in detail in Procedure S.

Chlorosulfonic acid is a well known reagent.

Compounds of general formula (XVII) may be prepared by the reaction of a compound of general formula (III) as defined above with benzaldehyde under similar conditions to those described for the reaction between the compounds of general formulae (III) and (IV). The reaction is described in procedure R below.

Compounds of general formula (I) are CRTH2 receptor antagonists and compounds of general formula (II) are pro-drugs for compounds of general formula (I). Compounds of general formulae (I) and (II) are therefore useful in a method for the treatment of diseases and conditions mediated by PGD$_2$ or other agonists at the CRTH2 receptor, the method comprising administering to a patient in need of such treatment a suitable amount of a compound of general formula (I) or (II).

In a third aspect of the invention, there is provided a compound of general formula (I) or (II) for use in medicine, particularly for use in the treatment or prevention of diseases and conditions mediated by PGD$_2$ or other CRTH2 receptor agonists.

Furthermore, there is also provided the use of a compound of general formula (I) or (II) in the preparation of an agent for the treatment or prevention of diseases and conditions mediated by CRTH2 receptor agonists, particularly PGD$_2$.

As mentioned above, such diseases and conditions include allergic diseases, asthmatic conditions and inflammatory diseases, examples of which are asthma, including allergic asthma, bronchial asthma, intrinsic, extrinsic, exercise-induced, drug-induced and dust-induced asthma, treatment of cough, including chronic cough associated with inflammatory and secretory conditions of the airways and iatrogenic cough, acute and chronic rhinitis, including rhinitis medicamentosa, vasomotor rhinitis, perennial allergic rhinitis, seasonal allergic rhinitis, nasal polyposis, acute viral infection including common cold, infection due to respiratory syncytial virus, influenza, coronavirus and adenovirus, atopic dermatitis, contact hypersensitivity (including contact dermatitis), eczematous dermatitis, phyto dermatitis, photo dermatitis, sebhorroeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa urticaria, angioedema, vasculitides, toxic erythemas, cutaneous eosinophilias, alopecia areata, male-pattern baldness, Sweet's syndrome, Weber-Christian syndrome, erythema multiforme, cellulitis, panniculitis, cutaneous lymphomas, non-melanoma skin cancer and other dysplastic lesions; blepharitis conjunctivitis, especially allergic conjunctivitis, anterior and posterior uveitis, choroiditis, autoimmune, degenerative or inflammatory disorders affecting the retina, ophthalmitis; bronchitis, including infectious and eosinophilic bronchitis, emphysema, bronchiectasis, farmer's lung, hypersensitivity pneumonitis, idiopathic interstitial pneumonias, complications of lung transplantation, vasculitic and thrombotic disorders of the lung vasculature, pulmonary hypertension, food allergies, gingivitis, glossitis, periodontitis, oesophagitis including reflux, eosinophilic gastroenteritis, proctitis, pruris ani, celiac disease, food-related allergies, inflammatory bowel disease, ulcerative colitis and Crohn's disease, mastocytosis and also other CRTH2-mediated diseases, for example autoimmune diseases such as hyper IgE syndrome, Hashimoto's thyroiditis, Graves' disease, Addison's disease, diabetes mellitus, idiopathic thrombocytopaenic purpura, eosinophilic paschiitis, antiphospholipid syndrome and systemic lupus erythematosus, AIDS, leprosy, Sezary syndrome, paraneoplastic syndrome, mixed and undifferentiated connective tissue diseases, inflammatory myopathies including dermatomyositis and polymyositis, polymalgia rheumatica, juvenile arthritis, rheumatic fever, vasculitides including giant cell arteritis, Takayasu's arteritis, Churg-Strauss syndrome, polyarteritis nodosa, microscopic polyarteritis, temporal arteritis, myasthenia gravis, acute and chronic pain, neuropathic pain syndromes, central and peripheral nervous system complications of malignant, infectious or autoimmune processes, low back pain, familial Mediterranean Fever, Muckle-Wells syndrome, Familial Hibernian fever, Kikuchi disease, psoriasis, acne, multiple sclerosis, allograft rejection, reperfusion injury, chronic obstructive pulmonary disease, as well as rheumatoid arthritis, Still's disease, ankylosing spondylitis, reactive arthritis, undifferentiated spondarthropathy, psoriatic arthritis, septic arthritis and other infection-related arthopathies and bone disorders and osteoarthritis; acute and chronic crystal-induced synovitis including urate gout, calcium pyrophosphate deposition disease, calcium paptite related tendon syndrome and synovial inflammation, Behcet's disease, primary and secondary Sjogren's syndrome systemic sclerosis and limited scleroderma; hepatitis, cirrhosis of the liver, cholecystitis, pancreatitis, nephritis, nephritic syndrome, cystitis and Hunner's ulcer, acute and chronic urethritis, prostatitis, epididymitis, oophoritis, salpingitis, vulvo-vaginitis, Peyronie's disease, erectile dysfunction, Alzheimer's disease and other dementing disorders; pericarditis, myocarditis, inflammatory and auto-immune cardiomyopathies including myocardial sarcoid, ischaemic reperfusion injuries, endocarditis, valvulitis, aortitis, phlebitis, thrombosis, treatment of common cancers and fibrotic conditions such as idiopathic pulmonary fibrosis including cryptogenic fibrosing alveolitis, keloids, excessive fibrotic scarring/adhesions post surgery, liver fibrosis including that associated with hepatitis B and C, uterine fibroids, sarcoidosis, including neurosarcoidosis, scleroderma, kidney fibrosis resulting from diabetes, fibrosis associated with RA, atherosclerosis, including cerebral atherosclerosis, vasculitis, myocardial fibrosis resulting from myocardial infarction, cystic fibrosis, restenosis, systemic sclerosis, Dupuytren's disease, fibrosis complicating anti-neoplastic therapy and chronic infection including tuberculosis and aspergillosis and other fungal infections, and CNS fibrosis following stroke. The compounds are also of use in the promotion of healing without fibrotic scarring.

The compounds are particularly effective when used for the treatment or prevention of allergic asthma, perennial allergic rhinitis, seasonal allergic rhinitis, atopic dermatitis, contact hypersensitivity (including contact dermatitis), conjunctivitis, especially allergic conjunctivitis, vernal keratoconjunctivitis and atopic keratoconjunctivitis, eosinophilic bronchitis, food allergies, eosinophilic gastroenteritis, inflammatory bowel disease, ulcerative colitis and Crohn's disease, mastocytosis and also other PGD2-mediated diseases, for example autoimmune diseases such as hyper IgE syndrome and systemic lupus erythematus, psoriasis, acne, multiple sclerosis, allograft rejection, reperfusion injury, chronic obstructive pulmonary disease, as well as rheumatoid arthritis, psoriatic arthritis, osteoarthritis and fibrotic diseases caused/exacerbated by Th2 immune responses, for example idiopathic pulmonary fibrosis and hypertrophic scars.

The compounds of general formula (I) or (II) must be formulated in an appropriate manner depending upon the diseases or conditions they are required to treat.

Therefore, in a further aspect of the invention there is provided a pharmaceutical composition comprising a compound of general formula (I) or (II) together with a pharmaceutical excipient or carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) or (II) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) or (II) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit $PGD_2$ at the CRTH2 receptor. The precise amount of a compound of general formula (I) or (II) which is therapeutically effective, and the route by which such compound is best administered, is readily determined by one of ordinary skill in the art by comparing the blood level of the agent to the concentration required to have a therapeutic effect.

Compounds of general formula (I) or (II) may be used in combination with one or more active agents which are useful in the treatment of the diseases and conditions listed above, although these active agents are not necessarily inhibitors of $PGD_2$ at the CRTH2 receptor.

Therefore, the pharmaceutical composition described above may additionally contain one or more of these active agents.

There is also provided the use of a compound of general formula (I) or (II) in the preparation of an agent for the treatment of diseases and conditions mediated by CRTH2 receptor agonists, especially $PGD_2$, wherein the agent also comprises an additional active agent useful for the treatment of the same diseases and conditions.

These additional active agents may be other CRTH2 receptor antagonists or may have a completely different mode of action. They include existing therapies for allergic and other inflammatory diseases including:

Suplatast tosylate and similar compounds;
β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol or methylxanthines such as theophylline and aminophylline, mast cell stabilisers such as sodium chromoglycate or muscarinic receptor antagonists such as tiotropium;
antihistamines, for example histamine $H_1$ receptor antagonists such as loratadine, cetirizine, desloratidine, levocetirizine, fexofenadine, astemizole, azelastine and chlorpheniramine or $H_4$ receptor antagonists;
$\alpha_1$ and $\alpha_2$ adrenoreceptor agonists such as propylhexedrine phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride; modulators of chemokine receptor function, for example CCR1, CCR2, CCR2A, CCR2B, CCR3, CCR4, CCR5, CCR6, CCR7, CCR8, CCR9, CCR10 and CCR11 (for the C—C family) or CXCR1, CXCR2, CXCR3, CXCR4 and CXCR5 (for the C—X—C family) and $CX_3CR1$ for the C—$X_3$—C family;
Leukotriene antagonists such as montelukast and zafirlukast leukotriene biosynthesis inhibitors such as 5-lipoxygenase inhibitors or 5-lipoxygenase activating protein (FLAP) inhibitors such as zileuton, ABT-761, fenleuton, tepoxalin, Abbott-79175, N-(5-substituted)-thiophene-2-alkylsolfonamides, 2,6-di-tert-butylphenol hydrazones, methoxytetrahydropyrans such as ZD2138, SB-210661, pyridinyl-substituted-2-cyanonaphthalene compounds such as L-739010, 2-cyanoquinoline compounds such as L-746,530, indole and quinoline compounds such as MK-591, MK-886 and BAY x 1005;
Phosphodiesterase inhibitors, including PDE4 inhibitors such as roflumilast;
anti-IgE antibody therapies such as omalizumab;
anti-infectives such as fusidic acid (particularly for the treatment of atopic dermatitis);
anti-fungals such as clotrimazole (particularly for the treatment of atopic dermatitis);
immunosuppressants such as tacrolimus and particularly pimecrolimus in the case of inflammatory skin disease or alternatively FK-506, rapamycin, cyclosporine, azathioprine or methotrexate;
Immunotherapy agents including allergen immunotherapy such as Grazax and in vivo and ex vivo approaches to increase the immunogenicity of patient tumour cells such as transfection with cytokines such as IL2, IL4 or GMCSF, approaches to decrease T-cell anergy, approaches using transfected immune cells such as cytokine-transfected dendritic cells or approaches using cytokine-transfected tumour cell lines or anti-idiotypic antibodies;
corticosteroids such as prednisone, prednisolone, flunisolide, triamcinolone acetonide, beclomethasone dipropionate, budesonide, fluticasone propionate mometasone furoate and fluticasone furoate drugs which promote Th1 cytokine response such as interferons, TNF or GM-CSF.

CRTH2 antagonists may also be combined with therapies that are in development for inflammatory indications including:
other antagonists of $PGD_2$ acting at other receptors such as DP antagonists;
inhibitors of phosphodiesterase type 4 such as roflumilast;
drugs that modulate cytokine production such as inhibitors of TNFα converting enzyme (TACE) anti-TNF monoclonal antibodies, TNF receptor immunoglobulin molecules, inhibitors of other TNF isoforms, non-selective COX-1/COX-2 inhibitors such as piroxicam, diclofenac, propionic acids such as naproxen, flurbiprofen, fenoprofen, ketoprofen and ibuprofen, fenamates such as mefanamic acid, indomethacin, sulindac and apazone, pyrazolones such as phenylbutazone, salicilates such as aspirin; COX-2 inhibitors such as meloxicam, celecoxib, fofecoxib, valdecoxib and etoricoxib, low dose methotrexate, lefunomide, ciclesonide, hydroxychloroquine, d-penicillamine, auranofin or parenteral or oral gold;
drugs that modulate the activity of Th2 cytokines IL-4 and IL-5 such as blocking monoclonal antibodies and soluble receptors;
PPAR-γ agonists such as rosiglitazone; or with
anti-RSV antibodies such as Synagis (palivizumab) and agents that may be used to treat rhinovirus infection in the future e.g. interferon-beta and other interferons.

In yet a further aspect of the invention, there is provided a product comprising a compound of general formula (I) or (II) and one or more of the agents listed above as a combined preparation for simultaneous, separate or sequential use in the treatment of a disease or condition mediated by the action of $PGD_2$ at the CRTH2 receptor.

In yet another aspect of the invention, there is provided a kit for the treatment of a disease or condition mediated by the action of $PGD_2$ at the CRTH2 receptor comprising a first container comprising a compound of general formula (I) or (II) and a second container comprising one or more of the active agents listed above.

The invention will now be described in greater detail with reference to the following non limiting examples.

In the Examples, the NMR spectra were obtained using a Bruker Advance II spectrometer operating at 300 MHz. All signals were referenced relative to residual protic solvent.

HPLC-CAD-MS was performed on a Gilson 321 HPLC with detection performed by a ESA Corona CAD and a Finnigan AQA mass spectrometer operating in positive- or negative-ion electrospray ionisation mode. The HPLC column was a Phenomenex Gemini C18 50×4.6 mm 3μ, with a mobile phase gradient between 100% 0.1% formic acid in water and 100% 0.1% formic acid, with the total run time being stated in parenthesis after the retention time of the compound.

Compounds were prepared according to the General Procedures outlined in Schemes 1, 2 and 3 and described below.

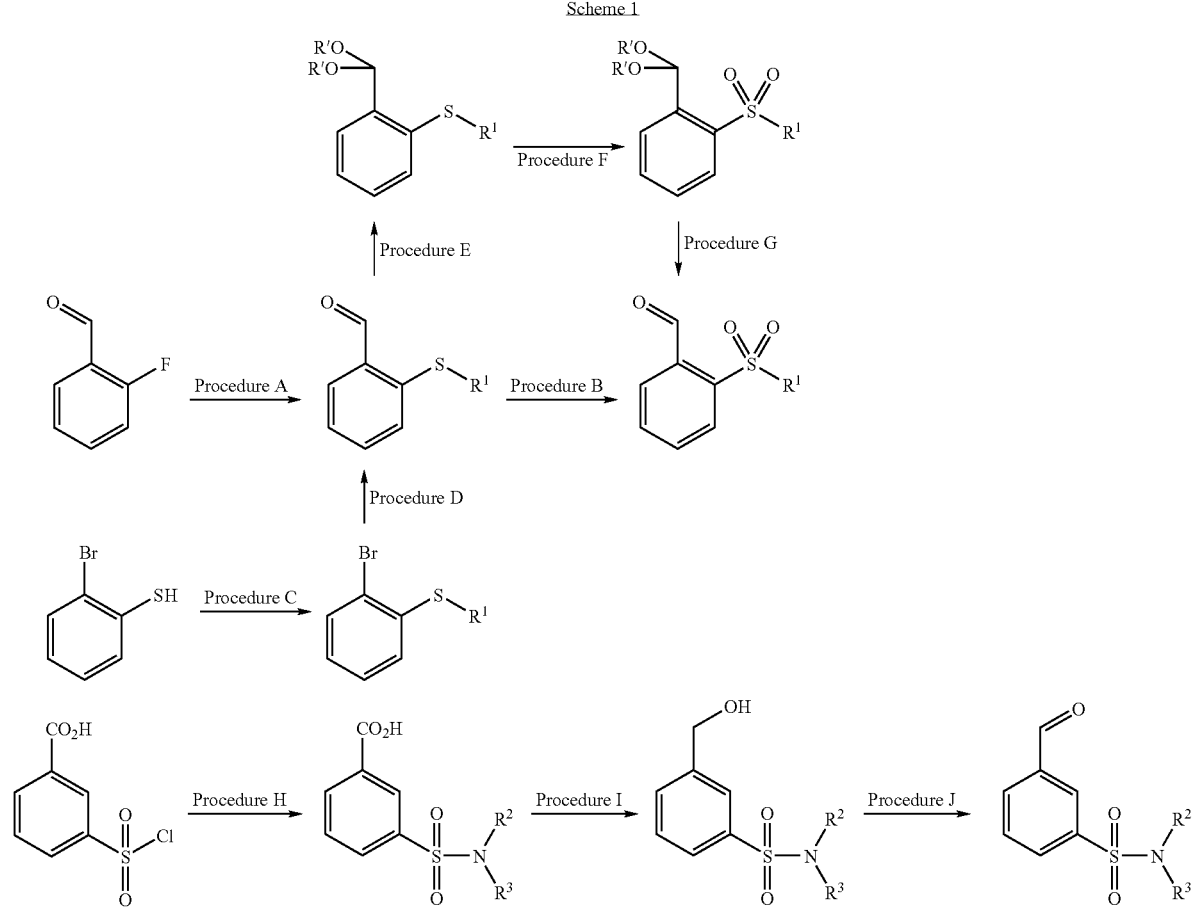

Scheme 1

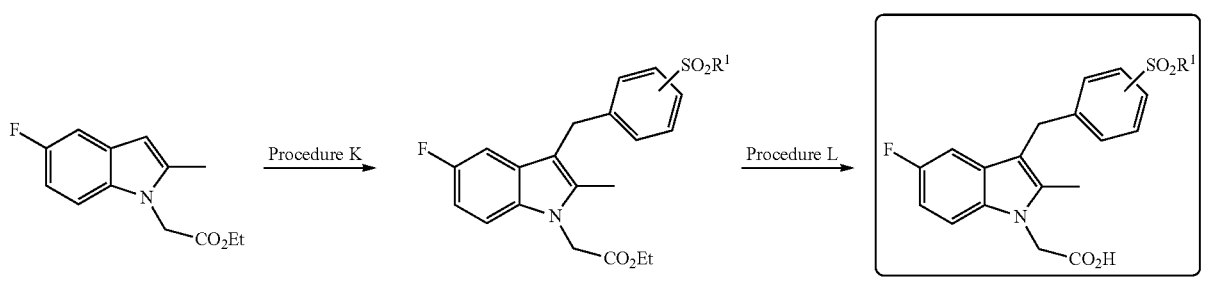

Scheme 2

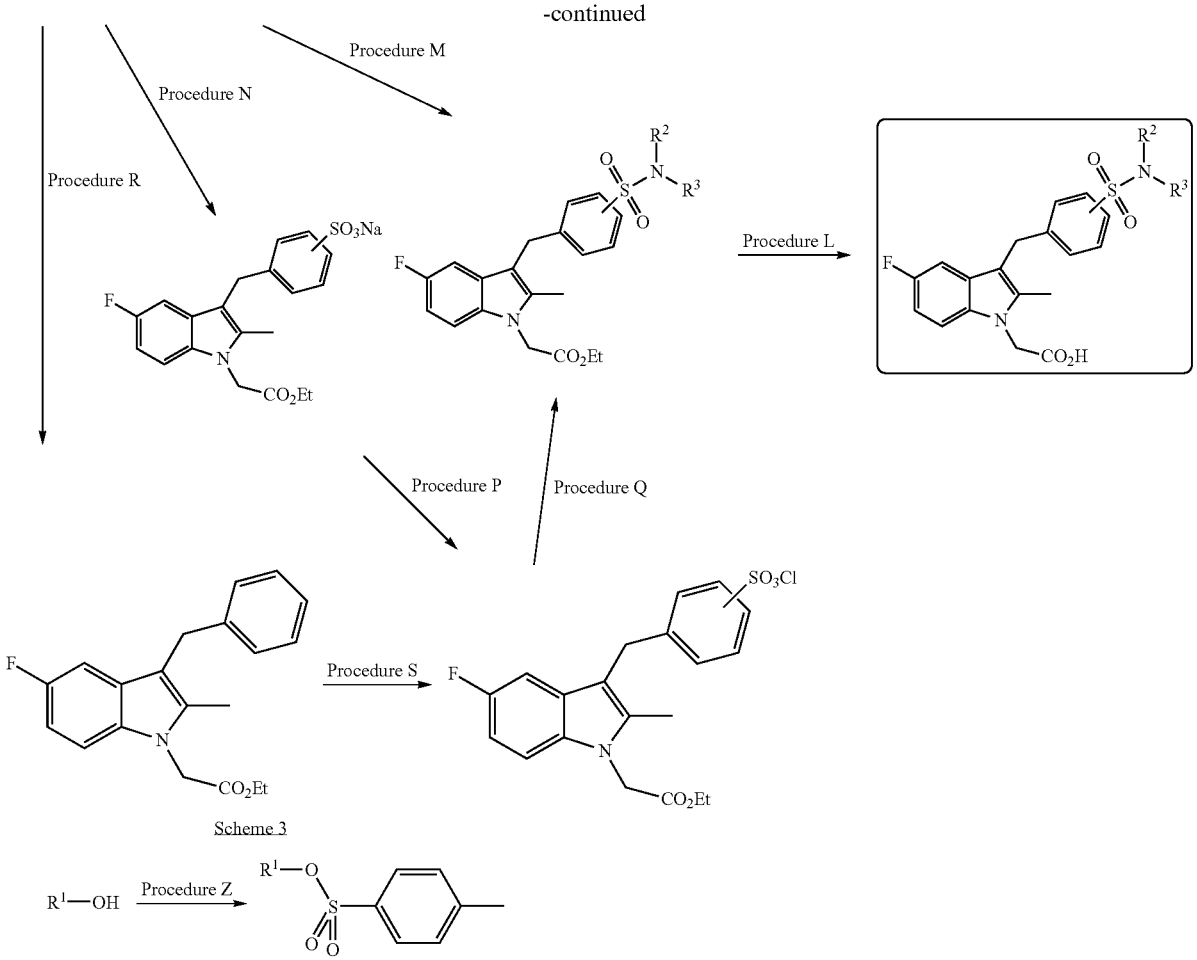

Scheme 3

2-(3-(2-(Cyclohexylsulfonyl)benzyl)-5-fluoro-2-methyl-1H-indol-1-yl)acetic acid (Compound 1)

Procedure A: 2-(Cyclohexylthio)benzaldehyde

To a stirred suspension of $K_2CO_3$ (4.5 g, 32.6 mmol) and cyclohexylmercaptan (2.0 mL, 16.4 mmol) in DMSO (20 mL) was added 2-fluorobenzaldehyde (1.7 mL, 16.2 mmol) dropwise over 10 minutes at room temperature, and the reaction mixture was heated at 100° C. for 5 hours with stirring. After cooling to room temperature, the reaction mixture was partitioned between ethyl acetate and water. The organic layer was separated and the aqueous phase extracted with ethyl acetate (×3). The combined organic extracts were washed successively with sodium bicarbonate solution and brine, then dried over anhydrous magnesium sulfate, filtered and evaporated in vacuo to afford 2-(cyclohexylthio)benzaldehyde (3.22 g, 14.6 mmol, 90%) which was used directly without further purification.

$^1$H NMR (CDCl$_3$): 10.60 (1H, s), 7.92-7.88 (1H, m), 7.55-7.53 (2H, m), 7.40-7.35 (1H, m), 3.15-3.13 (1H, m), 2.03-1.99 (2H, m), 1.84-1.78 (2H, m), 1.69-1.60 (1H, m), 1.45-1.29 (5H, m).

Procedure B: 2-(Cyclohexylsulfonyl)benzaldehyde

To a solution of 2-(cyclohexylthio)benzaldehyde (3.22 g, 14.6 mmol) in DCM (100 mL) at 0° C. was added mCPBA (70-77% wt in water, 7.17 g, 30.7 mmol) portionwise over 30 minutes, then stirred for 1 hour at 0° C. Additional mCPBA (150 mg, 0.6 mmol) was added and stirred for a further 30 minutes, before aqueous 1N NaOH was added to the reaction mixture and stirred vigorously for 5 minutes. The product was extracted with DCM, and the combined organic phase washed successively with 1N NaOH, then saturated brine, dried over anhydrous magnesium sulfate, filtered and evaporated in vacuo to afford 2-(cyclohexylsulfonyl)benzaldehyde (3.34 g, 13.2 mmol, 91%) as a white solid.

$^1$H NMR (CDCl$_3$): 10.85 (1H, s), 8.13-8.10 (1H, m), 8.05-8.02 (1H, m), 7.80-7.77 (2H, m), 3.00 (1H, tt, J 12.1 & 3.5 Hz), 2.06-1.90 (2H, m), 1.88-1.86 (2H, m), 1.71-1.70 (1H, m), 1.52-1.30 (2H, m), 1.26-1.18 (3H, m).

Procedure K: 2-(3-(2-(Cyclohexylsulfonyl)benzyl)-5-fluoro-2-methyl-1H-indol-1-yl)acetic Acid Ethyl Acetate To a stirred solution of [5-fluoro-2-methyl-1H-indol-1-yl] acetic acid ethyl ester (0.85 g, 3.62 mmol) at room temperature in dichloromethane (20 mL) was added 2-(cyclohexylsulfonyl)benzaldehyde (1.00 g, 3.97 mmol) followed by triethylsilane (2.9 mL, 18.3 mmol). TFA (0.85 mL, 11.0 mmol) was then added dropwise over 15 minutes, and after the addition was complete, the resulting mixture was stirred for 2 hours. Saturated aqueous NaHCO$_3$ was then added to the solution, and the separated organic layer was washed with brine, dried over anhydrous magnesium sulfate, filtered and evaporated in vacuo. The resulting solid was purified by trituration with light petroleum then recrystallised from an ethyl acetate/hexanes mixture to afford ethyl 2-(3-(2-(cyclohexylsulfonyl)benzyl)-5-fluoro-2-methyl-1H-indol-1-yl)acetate (0.875 g, 1.86 mmol, 51%).

LCMS RT=7.74 min (12.5 min run time), MH+ 472.2

$^1$H NMR (CDCl$_3$): 8.02 (1H, dd, J 7.7 & 1.6 Hz), 7.48-7.34 (2H, m), 7.20 (1H, dd, J 7.5 & 1.3 Hz), 7.13 (1H, dd, J 8.8 & 4.3 Hz), 6.94-6.81 (2H, m), 4.82 (2H, s), 4.54 (2H, s), 4.24 (2H, q, J 7.1 Hz), 2.90 (1H, tt, J 12.0 & 3.4 Hz), 2.35 (3H, s), 2.03-1.92 (2H, m), 1.91-1.81 (2H, m), 1.72-1.51 (3H, m), 1.28 (3H, t, J 7.1 Hz), 1.22-1.02 (3H, m).

Procedure L: 2-(3-(2-(Cyclohexylsulfonyl)benzyl)-5-fluoro-2-methyl-1H-indol-1-yl)acetic Acid (Compound 1)

To a stirred solution of 2-(3-(2-(cyclohexylsulfonyl)benzyl)-5-fluoro-2-methyl-1H-indol-1-yl)acetic acid ethyl ester (0.875 g, 1.86 mmol) in THF (15 mL) was added a solution of potassium hydroxide (0.31 g, 5.57 mmol) in water (15 mL), and the resulting solution stirred at room temperature for 2 hours. The THF was then removed in vacuo and the remaining aqueous layer diluted with water, then washed with dichloromethane. The remaining aqueous layer was acidified with aqueous 3N HCl and extracted with ethyl acetate (×3). The combined organic extracts were washed with brine, dried over anhydrous magnesium sulfate, filtered and the volatiles removed in vacuo to afford 0.73 g of white solid. This material was dissolved in a solution of potassium carbonate (0.75 g, 4.45 mmol) in water (30 mL) and stirred until completely dissolved before acidifying with a solution of citric acid (20% w/v) until effervescence ceased. The resulting precipitate was filtered, washed several times with water and dried in vacuo to afford 2-(3-(2-(cyclohexylsulfonyl)benzyl)-5-fluoro-2-methyl-1H-indol-1-yl)acetic acid (0.463 g, 1.04 mmol, 56%).

LCMS RT=4.82 mins (12.5 min run time), M-H+442.2

$^1$H NMR (d$_6$ DMSO): 7.89 (1H, dd, J 7.7 & 1.3 Hz), 7.58 (1H, td, J 7.5 & 1.6 Hz), 7.47 (1H, td, J 7.5 & 1.3 Hz), 7.38 (1H, dd, J 8.8 & 4.4 Hz), 7.22 (1H, d, J 7.5 Hz), 6.93-6.82 (2H, m), 4.92 (2H, s), 4.50 (2H, s), 3.05 (1H, tt, J 12.0 & 3.3 Hz), 2.31 (3H, s), 1.82-1.68 (4H, m), 1.63-1.52 (1H, m), 1.46-1.30 (2H, m), 1.20-1.04 (3H, m).

2-(5-Fluoro-2-methyl-3-(2-(piperidin-1-ylsulfonyl)benzyl)-1H-indol-1-yl)acetic Acid (Compound 2)

Procedure N: Sodium 2-((1-(2-ethoxy-2-oxoethyl)-5-fluoro-2-methyl-1H-indol-3-yl)methyl)benzenesulfonate To a stirred solution of [5-fluoro-2-methyl-1H-indol-1-yl] acetic acid ethyl ester (2.16 g, 9.19 mmol) at room temperature in dichloromethane (80 mL), was added 2-formylbenzenesulfonic acid sodium salt hydrate (2.01 g, 9.66 mmol) followed by triethylsilane (7.6 mL, 47.8 mmol). TFA (2.24 mL, 29.1 mmol) was then added dropwise over 30 min, and after the addition was complete, the mixture was stirred at room temperature for 72 h. Saturated aqueous NaHCO$_3$ (100 mL) was then added to the solution plus saturated brine (10 mL) and the product extracted with ethyl acetate (200 ml). The organic layer was washed with saturated brine (100 mL), dried over anhydrous magnesium sulfate, filtered and evaporated in vacuo. The resulting pink sticky solid was triturated with ethanol and hexanes to give sodium 2-((1-(2-ethoxy-2-oxoethyl)-5-fluoro-2-methyl-1H-indol-3-yl)methyl)benzene-sulfonate (2.33 g, 5.45 mmol, 59%).

$^1$H NMR (d$_6$ DMSO): 7.81-7.76 (1H, m), 7.33 (1H, dd, J 8.9, 4.4 Hz), 7.16-7.01 (3H, m), 6.83 (1H, td, J 9.4, 2.6 Hz), 6.75-6.68 (1H, m), 5.08 (2H, s), 4.45 (2H, s), 4.15 (2H, q, J 7.1 Hz), 2.29 (3H, s), 1.20 (3H, t, J 7.1 Hz).

Procedure P: Ethyl 2-(3-(2-(chlorosulfonyl)benzyl)-5-fluoro-2-methyl-1H-indol-1-yl)acetate Sodium 2-((1-(2-ethoxy-2-oxoethyl)-5-fluoro-2-methyl-1H-indol-3-yl)methyl)benzenesulfonate (2.30 g, 5.38 mmol) was added portionwise to chlorosulfonic acid (10 ml) at room temperature (20° C.) over 20 min. The resulting mixture was stirred at room temperature for 2 hours, then poured onto ice/water (300 mL). The solution was next extracted with CH$_2$Cl$_2$, and the separated organics washed with water, dried over anhydrous magnesium sulfate, filtered and evaporated in vacuo to afford ethyl 2-(3-(2-(chlorosulfonyl)benzyl)-5-fluoro-2-methyl-1H-indol-1-yl)acetate (2.03 g, 4.79 mmol, 89%), which was used in the next step without further purification.

$^1$H NMR (CDCl$_3$): 8.16 (1H, dd, J 1.5, 8.0 Hz), 7.53-7.37 (2H, m), 7.19-7.08 (2H, m), 6.98-6.88 (2H, m), 4.85 (2H, s), 4.64 (2H, s), 4.25 (2H, q, J 7.2 Hz), 2.33 (3H, s), 1.30 (3H, t, J 7.2 Hz).

Procedure Q: Ethyl 2-(5-fluoro-2-methyl-3-(2-(piperidin-1-ylsulfonyl)benzyl)-1H-indol-1-yl)acetate To a stirred solution of piperidine (0.36 mL, 3.6 mmol) in pyridine (50 mL) was added 2-(3-(2-(chlorosulfonyl)benzyl)-5-fluoro-2-methyl-1H-indol-1-yl)acetic acid ethyl ester (1.53 g, 3.6 mmol), and the resulting solution stirred at room temperature for 18 h. The mixture was then diluted with water and extracted with ethyl acetate. The organic layer was washed with saturated copper sulfate solution (×3), dried over anhydrous magnesium sulfate, filtered and evaporated in vacuo to afford 2-(5-fluoro-2-methyl-3-(2-(piperidin-1-ylsulfonyl)benzyl)-1H-indol-1-yl)acetic acid ethyl ester (1.23 g, 2.60 mmol, 72%) as a yellow oil, which was used in the next step without further purification.

$^1$H NMR (CDCl$_3$): 8.04-7.98 (1H, m), 7.37-7.25 (2H, m), 7.14 (1H, dd, J 4.2 & 8.6 Hz) 7.03-6.97 (1H, m), 6.97-6.86 (2H, m), 4.83 (2H, s), 4.49 (2H, s), 4.24 (2H, q, J 7.2 Hz), 3.34-3.26 (4H, m), 2.31 (3H, s), 1.76-1.53 (6H, m), 1.29 (3H, t, J 7.2 Hz).

Procedure L: 2-(5-Fluoro-2-methyl-3-(2-(piperidin-1-ylsulfonyl)benzyl)-1H-indol-1-yl)acetic Acid (Compound 2)

To a stirred solution of 2-(5-fluoro-2-methyl-3-(2-(piperidin-1-ylsulfonyl)benzyl)-1H-indol-1-yl)acetic acid ethyl ester (1.23 g, 2.60 mmol) in THF (50 mL), was added a solution of potassium hydroxide (0.73 g, 13.0 mmol) in water (50 mL), and the resulting solution stirred at room temperature for 2 hours. Aqueous HCl (2N, 15 mL) was then added and the aqueous layer extracted with ethyl acetate (100 mL). The organic layers were washed with brine (2×50 mL), dried over anhydrous magnesium sulfate, filtered and evaporated in vacuo. The solid was triturated with diethyl ether and dried in vacuo to afford 2-(5-fluoro-2-methyl-3-(2-(piperidin-1-ylsulfonyl)benzyl)-1H-indol-1-yl)acetic acid (1.09 g, 2.45 mmol, 94%).

LCMS RT=4.65 mins (12.5 mins run time), M-H⁺ 443.2
¹H NMR (d₆ DMSO): 7.90-7.84 (1H, m), 7.48-7.34 (3H, m), 7.00-6.83 (3H, m), 5.00 (2H, s), 4.37 (2H, s), 3.22-3.13 (4H, m), 2.27 (3H, s), 1.65-1.46 (6H, m).

2-(3-(2-(Cyclopentylsulfonyl)benzyl)-5-fluoro-2-methyl-1H-indol-1-yl)acetic Acid (Compound 3)

Cyclopentylthiol was used as starting material in Procedure A, otherwise this compound was prepared in a similar manner to Compound 1, using Procedures A, B, K & L.
LCMS RT=4.72 mins (12.5 mins run time), M-H⁺ 428.2
¹H NMR (d₆ DMSO): 13.00 (1H, br), 7.94 (1H, dd, J 7.7 & 1.5 Hz), 7.55-7.36 (3H, m), 7.09 (1H, dd, J 7.6 & 1.2 Hz), 6.95 (1H, dd, J 10.2 & 2.7 Hz), 6.87 (1H, td, J 9.2 & 2.4 Hz), 5.00 (2H, s), 4.50 (2H, s), 3.93-3.82 (1H, m), 2.28 (3H, s), 1.95-1.51 (8H, m).

2-(5-Fluoro-2-methyl-3-(3-(piperidin-1-ylsulfonyl)benzyl)-1H-indol-1-yl)acetic Acid (Compound 4)

Procedure H: 3-(Piperidin-1-ylsulfonyl)benzoic Acid

To a stirred solution of 3-(chlorosulfonyl)benzoic acid (1.10 g, 5.00 mmol) in DCM (10 mL) was added piperidine (1.49 g, 17.5 mmol) at 0° C., and the resulting solution stirred for 30 minutes. The volatiles were then removed in vacuo and the residue treated with aqueous 1N KHSO₄. The aqueous phase was then extracted with ethyl acetate (×3), and the combined organic phases dried over anhydrous magnesium sulfate, filtered and evaporated in vacuo to afford 3-(piperidin-1-ylsulfonyl)benzoic acid (1.22 g, 4.52 mmol, 90%).
¹H NMR (d₆ DMSO): 13.54 (1H, br), 8.24 (1H, dt, J 8.0 & 1.4 Hz), 8.18 (1H, t, J 1.8 Hz), 7.97 (1H, dt, J 8.0 & 1.6 Hz), 7.79 (1H, t, J 7.7 Hz), 2.93-2.88 (4H, m), 1.58-1.50 (4H, m), 1.40-1.32 (2H, m).

Procedure I:
(3-(Piperidin-1-ylsulfonyl)phenyl)methanol

To a solution of 3-(piperidin-1-ylsulfonyl)benzoic acid (538 mg, 2.00 mmol) in dry THF (8 mL) under nitrogen was added a solution of borane-THF complex in dry THF (1.0 M, 8 mL, 8.00 mmol) and the mixture then stirred for 18 hours at room temperature. The reaction was then quenched by the addition of excess methanol and evaporated in vacuo. The residue was partitioned between ethyl acetate and 2N HCl, and the separated organic layer washed successively with water and saturated brine, before being dried over anhydrous magnesium sulfate, filtered and evaporated in vacuo. The residue was purified using automated flash column chromatography on silica gel (gradient of 0 to 60% ethyl acetate in petrol) to afford (3-(piperidin-1-ylsulfonyl)phenyl)methanol (320 mg, 1.25 mmol, 63%).
¹H NMR (d₆ DMSO): 7.69-7.67 (1H, m), 7.64-7.57 (3H, m), 5.44 (1H, t, J 5.9 Hz), 4.60 (2H, d, J 5.3 Hz), 2.89-2.84 (4H, m), 1.58-1.50 (4H, m), 1.39-1.30 (2H, m).

Procedure J: 3-(Piperidin-1-ylsulfonyl)benzaldehyde

A solution of (3-(piperidin-1-ylsulfonyl)phenyl)methanol (160 mg, 0.627 mmol) in acetonitrile (5 mL) was added dropwise over 3 minutes to a stirred, ice-cold solution of pyridinium chlorochromate (203 mg, 0.944 mmol) in acetonitrile (5 mL). On completion of the addition the mixture was allowed to attain room temperature, and then heated to reflux for 1 hour. After cooling to ambient temperature and concentrating in vacuo, the residue was then taken up with a mixture of ethyl acetate and saturated sodium bicarbonate solution. The biphasic mixture was transferred to a separating funnel and further partitioned using brine solution. The separated organic phase was passed through a short pad of silica gel, dried over anhydrous magnesium sulfate, filtered and evaporated in vacuo to afford 3-(piperidin-1-ylsulfonyl)benzaldehyde (130 mg, 0.51 mmol, 81%) which was used directly without further purification.
¹H NMR (CDCl₃): 10.03 (1H, s), 8.17 (1H, t, J 1.6 Hz), 8.05 (1H, dt, J 7.6 1.3 Hz), 7.94 (1H, dt, J 7.6 1.3 Hz), 7.66 (1H, t, J 7.7 Hz), 2.98-2.93 (4H, m), 1.62-1.54 (4H, m), 1.41-1.32 (2H, m).

Procedure K: 2-(5-Fluoro-2-methyl-3-(3-(piperidin-1-ylsulfonyl)benzyl)-1H-indol-1-yl)acetic Acid Ethyl Ester 3-(Piperidin-1-ylsulfonyl)benzaldehyde was used as the starting material, otherwise this compound was prepared in a similar manner Compound 1, using Procedure K.
¹H NMR (d₆ DMSO): 7.59-7.55 (1H, m), 7.51 (1H, s), 7.45-7.37 (2H, m), 7.13-7.07 (1H, m), 6.90-6.83 (2H, m), 4.81 (2H, s), 4.23 (2H, q, J 7.2 Hz), 4.13 (2H, s), 2.83-2.79 (4H, m), 2.37 (3H, s), 1.58-1.50 (4H, m), 1.40-1.32 (2H, m), 1.28 (3H, t, J 7.2 Hz).

Procedure L: 2-(5-Fluoro-2-methyl-3-(3-(piperidin-1-ylsulfonyl)benzyl)-1H-indol-1-yl)acetic acid (Compound 4)

2-(5-fluoro-2-methyl-3-(3-(piperidin-1-ylsulfonyl)benzyl)-1H-indol-1-yl)acetic acid ethyl ester was used as a starting material, otherwise this compound was prepared in a similar manner to Compound 1, using Procedure L.
LCMS RT=4.31 mins (12.5 min run time), M-H⁺ 443.2
¹H NMR (DMSO): 12.90 (1H, br), 7.58-7.47 (4H, m), 7.36 (1H, dd, J 9.0 & 4.6 Hz), 7.06 (1H, dd, J 9.7 & 2.5 Hz), 6.85 (1H, td, J 9.3 & 2.4 Hz), 4.97 (2H, s), 4.14 (2H, s), 2.74-2.68 (4H, m), 2.34 (3H, s), 1.47-1.39 (4H, m), 1.30-1.21 (2H, m).

2-(5-Fluoro-2-methyl-3-(2-(pyrrolidin-1-ylsulfonyl)benzyl)-1H-indol-1-yl)acetic Acid (Compound 5)

Pyrrolidine was used as starting material in Procedure Q, otherwise this compound was prepared in a similar manner to Compound 2, using Procedures N, P, Q & L.
LCMS RT=4.59 mins (12.5 min run time), M-H⁺ 429.2
¹H NMR (d₆DMSO): 7.85 (1H, dd, J 7.7 & 1.6), 7.48-7.34 (3H, m), 6.99 (1H, dd, J 7.6 & 1.4), 6.96-6.83 (2H, m), 4.99 (2H, s), 4.39 (2H, s), 3.38-3.27 (4H, m, obscured by water peak), 2.27 (3H, s), 1.93-1.86 (4H, m).

2-(3-(4-(Cyclohexylsulfonyl)benzyl)-5-fluoro-2-methyl-1H-indol-1-yl)acetic Acid (Compound 6)

Procedure A: 4-(Cyclohexylthio)benzaldehyde

4-Fluorobenzaldehyde was used as a starting material, otherwise this compound was prepared in a similar manner to Compound 1, following Procedure A.
¹H NMR (CDCl₃): 9.97 (1H, s), 7.81 (2H, d, J 8.3 Hz), 7.44 (2H, d, J 8.4 Hz), 3.44-3.36 (1H, m), 2.12-2.09 (2H, m), 1.88-1.84 (2H, m), 1.73-1.68 (1H, m), 1.57-1.32 (5H, m).

Procedure E:
Cyclohexyl(4-(dimethoxymethyl)phenyl)sulfane

To a solution of 4-(cyclohexylthio)benzaldehyde (215 mg, 0.976 mmol) in methanol (4 mL) was added trimethylorthoformate (130 μL, 1.19 mmol) and p-toluenesulfonic acid (15 mg, 0.079 mmol), and the resulting solution stirred at room temperature for 72 hours. Sodium methoxide solution (25 wt %, 18 μL) was then added to the solution, and the volatiles removed in vacuo to afford crude cyclohexyl(4-(dimethoxymethyl)phenyl)sulfane (~265 mg, quantitative yield) which was used directly without further purification.

$^1$H NMR (CDCl$_3$): 7.38-7.37 (4H, m), 5.37 (1H, s), 3.33 (6H, s), 3.32-3.12 (1H, m), 2.02-1.97 (2H, m), 1.78-1.75 (2H, m), 1.64-1.59 (1H, m), 1.40-1.26 (5H, m).

Procedure F:
1-(Cyclohexylsulfonyl)-4-(dimethoxymethyl)benzene

To a solution of cyclohexyl(4-(dimethoxymethyl)phenyl) sulfane (265 mg, 0.996 mmol) in ethyl acetate (6 mL) at −78° C. was added a solution of periodic acid (480 mg, 2.10 mmol) and chromium trioxide (10 mg, 0.10 mmol) in acetonitrile (4 mL) dropwise over 30 minutes. On completion of the addition an aqueous solution of sodium sulfite was added and the mixture allowed to warm to room temperature. The solution was then extracted with ethyl acetate (×4), and the separated organic phase washed with brine, dried over anhydrous magnesium sulfate, filtered and evaporated in vacuo. The residue was then purified using flash column chromatography on silica gel (gradient of 10 to 20% ethyl acetate in petrol) to afford 1-(cyclohexylsulfonyl)-4-(dimethoxymethyl)benzene (117 mg, 0.392 mmol, 39%).

$^1$H NMR (CDCl$_3$): 7.87 (2H, d, J 8.4 Hz), 7.65 (2H, d, J 8.1 Hz), 5.45 (1H, s), 3.34 (6H, s), 2.93-2.85 (1H, m), 2.08-2.03 (2H, m), 1.88-1.83 (2H, m), 1.68-1.64 (1H, m), 1.46-1.33 (2H, m), 1.28-1.12 (3H, m).

Procedure G: 4-(Cyclohexylsulfonyl)benzaldehyde

To a solution of 1-(cyclohexylsulfonyl)-4-(dimethoxymethyl)benzene (117 mg, 0.392 mmol) in THF (4 mL) was added an aqueous solution of sulfuric acid (2% v/v, 2 mL) and the resulting mixture stirred for 18 hours at room temperature. Excess solid potassium carbonate was then added, and the mixture diluted with water. Finally, the aqueous solution was extracted with ethyl acetate (×3), and the combined organic phases dried over anhydrous magnesium sulfate, filtered and evaporated in vacuo to give 4-(cyclohexylsulfonyl)benzaldehyde (1100 mg, quantitative yield) as a colourless oil.

$^1$H NMR (CDCl$_3$): 10.15 (1H, s), 8.10-8.04 (4H, m), 3.00-2.92 (1H, m), 2.09-2.06 (2H, m), 1.91-1.87 (2H, m), 1.72-1.69 (1H, m), 1.50-1.38 (2H, m), 1.31-1.13 (3H, m).

Procedure K: 2-(3-(4-(Cyclohexylsulfonyl)benzyl)-5-fluoro-2-methyl-1H-indol-1-yl)acetic acid ethyl ester 4-(Cyclohexylsulfonyl)benzaldehyde was used a starting material, otherwise this compound was prepared using a similar method to Compound 1, following Procedure K.

$^1$H NMR (CDCl$_3$): 7.73 (2H, d, J 8.4 Hz), 7.34 (2H, d, J 8.5 Hz), 7.12-7.09 (1H, m), 6.98-6.87 (2H, m), 4.81 (2H, s), 4.23 (2H, q, J 7.1 Hz), 4.14 (2H, s), 2.90-2.82 (1H, m), 2.34 (3H, s), 2.06-2.03 (2H, m), 1.87-1.83 (2H, m), 1.68-1.58 (1H, m), 1.41-1.29 (2H, m), 1.28 (3H, t, J 7.1 Hz), 1.27-1.14 (3H, m).

Procedure L: 2-(3-(4-(Cyclohexylsulfonyl)benzyl)-5-fluoro-2-methyl-1H-indol-1-yl)acetic Acid (Compound 6)

2-(3-(4-(Cyclohexylsulfonyl)benzyl)-5-fluoro-2-methyl-1H-indol-1-yl)acetic acid ethyl ester was used as the starting material, otherwise this compound was prepared in a similar manner to Compound 1, using Procedure L.

LCMS RT=2.17 min (4.5 min run time), MH$^+$ 444.3

$^1$H NMR (CDCl$_3$): 8.41-6.77 (1H, br s), 7.74-7.69 (2H, app. d), 7.36-7.30 (2H, app. d), 7.10 (1H, dd, J 8.8 & 4.2 Hz), 6.99-6.86 (2H, m), 4.85 (2H, s), 4.12 (2H, s), 2.86 (1H, tt, J 12.0 & 3.3 Hz), 2.34 (3H, s), 2.05-1.98 (1H, m), 1.86-1.82 (2H, m), 1.69-1.59 (1H, m), 1.46-1.30 (2H, m), 1.27-1.03 (4H, m).

2-(3-(4-(Cyclopentylsulfonyl)benzyl)-5-fluoro-2-methyl-1H-indol-1-yl)acetic Acid (Compound 7)

Cyclopentylthiol was used a starting material in Procedure A, otherwise this compound was prepared in a similar manner to Compound 6, using Procedures A, E, F, G, K & L.

LCMS RT=4.15 mins (12.5 min run time), MH$^+$ 429.7

$^1$H NMR (DMSO): 7.77-7.73 (2H, m), 7.49-7.44 (2H, m), 7.35 (1H, dd, J 8.8 & 4.5 Hz), 7.13 (1H, dd, J 9.9 & 2.5 Hz), 6.86 (1H, td, J 9.2 & 2.6 Hz), 4.94 (2H, s), 4.13 (2H, s), 3.73-3.66 (1H, m), 2.32 (3H, s), 1.86-1.69 (4H, m) and 1.64-1.45 (4H, m).

2-(3-(2-(Cyclobutylsulfonyl)benzyl)-5-fluoro-2-methyl-1H-indol-1-yl)acetic Acid (Compound 8)

Procedure Z: Cyclobutyl 4-methylbenzenesulfonate

To a solution of cyclobutanol (1 g, 13.9 mmol) in pyridine (20 mL) was added p-toluenesulfonyl chloride (2.9 g, 15.3 mmol) and the solution stirred at room temperature for 4 hours. Aqueous HCl was then added, and the solution extracted with ethyl acetate (×3). The combined organic layers were washed successively with saturated aqueous copper (II) sulfate (×3) and brine, then dried over anhydrous magnesium sulfate, filtered and evaporated in vacuo. The residue was purified using flash column chromatography on silica gel (gradient of 0% to 5% ethyl acetate in petrol) to give cyclobutyl 4-methylbenzenesulfonate (2.05 g, 9.07 mmol, 65%) as a colourless oil.

$^1$H NMR (CDCl$_3$): 7.82-7.79 (2H, m), 7.36-7.33 (2H, m), 4.81-4.76 (1H, m), 2.46 (3H, s), 2.33-2.13 (4H, s), 1.78-1.75 (1H, m), 1.56-1.46 (1H, m).

Procedure C: (2-Bromophenyl)(cyclobutyl)sulfane

To a suspension of sodium hydride (60% in oil, 390 mg, 9.75 mmol) in anhydrous DMF (20 mL) was added 2-bromobenzenethiol (1.03 mL, 8.37 mmol) dropwise over 5 minutes. After stirring for 10 minutes at room temperature a solution of cyclobutyl 4-methylbenzenesulfonate (2.0 g, 8.85 mmol) in dry DMF (3 mL) was added dropwise. The resulting solution was then stirred for 2 hours at room temperature, and 2 hours at 50° C. Water was then added, and the mixture extracted with ethyl acetate (×3). The combined organics were washed with brine (×3), then dried over anhydrous magnesium sulfate, filtered and evaporated in vacuo. The residue was purified by flash column chromatography on silica gel (eluting with neat petrol) to give (2-bromophenyl)(cyclobutyl)sulfane (1.19 g, 4.89 mmol, 58%) as a colourless oil.

$^1$H NMR (CDCl$_3$): 7.53 (1H, dd, J 7.9 & 1.1 Hz), 7.26-7.23 (1H, m), 7.08 (1H, dd, J 7.9 & 1.3 Hz), 7.03-6.97 (1H, m), 4.00-3.90 (1H, m), 2.63-2.53 (2H, m), 2.24-2.02 (4H, m).

Procedure D: 2-(Cyclobutylthio)benzaldehyde

To a solution of n-butyllithium (7.35 mL of a 1.6 M solution in hexanes, 11.7 mmol) in dry THF (15 mL) at −78° C.

was added dropwise over 10 minutes a solution of (2-bromophenyl)(cyclobutyl)sulfane (1.19 g, 4.89 mmol) in dry THF (15 mL) and the resulting solution stirred at −78° C. for 30 minutes. Anhydrous DMF (1.14 mL, 14.7 mmol) was then added, and the solution stirred at −78° C. for 5 minutes, before allowing to warm to room temperature and stirring for a further 1 hour. Water was then added, and the volatiles removed in vacuo, before extracting the mixture with ethyl acetate (×3). The combined organics were washed with brine, then dried over anhydrous magnesium sulfate, filtered and evaporated in vacuo. The residue was purified using flash column chromatography on silica gel (eluting with a gradient of 0 to 5% ethyl acetate) to afford 2-(cyclobutylthio)benzaldehyde (450 mg, 2.34 mmol, 48%).

$^1$H NMR (CDCl$_3$): 10.32 (1H, s), 7.83 (1H, dd, J 7.6 & 1.5 Hz), 7.49 (1H, td, J 7.5 & 1.6 Hz), 7.32-7.24 (2H, m), 3.98-3.89 (1H, m), 2.61-2.49 (2H, m), 2.23-2.00 (4H, m).

Using 2-(cyclobutylthio)benzaldehyde as a starting material, Compound 8 was then prepared in a similar manner to Compound 1, following Procedures B, K & L.

LCMS RT=4.54 min (12.5 min run time), M-H$^+$ 414.2

$^1$H NMR (d$_6$DMSO): 13.02 (1H, s), 7.92 (1H, dd, J 7.9 & 1.5 Hz), 7.50 (1H, td, J 7.5 & 1.6 Hz), 7.46-7.36 (2H, m), 7.05 (1H, dd, J 7.7 & 1.1 Hz), 6.95 (1H, dd, J 9.9 & 2.5 Hz), 6.87 (1H, td, J 9.1 & 2.5 Hz), 5.01 (2H, s), 4.46 (2H, s), 4.35-4.21 (1H, m), 2.45-2.30 (2H, m), 2.27 (3H, s), 2.21-2.07 (2H, m), 2.01-1.86 (2H, m).

2-(5-Fluoro-2-methyl-3-(3-(pyrrolidin-1-ylsulfonyl)benzyl)-1H-indol-1-yl)acetic Acid (Compound 9)

Pyrrolidine was used a starting material in Procedure H, otherwise this compound was prepared in a similar manner to Compound 4, using Procedures H, I, J, K & L.

LCMS RT=4.50 mins (12.5 min run time), M-H$^+$ 429.2

$^1$H NMR (d$_6$DMSO): 7.64-7.46 (4H, m), 7.35 (1H, dd, J 8.9 & 4.4 Hz), 7.07 (1H, dd, 10.0&2.6 Hz), 6.86 (1H, td, J 9.4&2.7 Hz), 4.96 (2H, s), 4.14 (2H, s), 3.07-2.98 (4H, m), 2.33 (3H, s), 1.54-1.46 (4H, m).

2-(5-Fluoro-2-methyl-3-(4-(piperidin-1-ylsulfonyl)benzyl)-1H-indol-1-yl)acetic Acid (Compound 10)

Procedure R: 2-(3-Benzyl-5-fluoro-2-methyl-1H-indol-1-yl)acetic acid ethyl ester Benzaldehyde was used as a starting material, otherwise this compound was prepared in a similar manner to Compound 1, using Procedure K.

$^1$H NMR (CDCl$_3$): 7.25-7.17 (5H, m), 7.16-7.02 (2H, m), 6.91 (1H, td, J 9.1 & 2.5 Hz), 4.79 (2H, s), 4.22 (2H, q, J 7.1 Hz), 4.06 (2H, s), 2.34 (3H, s), 1.27 (3H, t, J 7.1 Hz)

Procedure S: 2-(3-(4-(Chlorosulfonyl)benzyl)-5-fluoro-2-methyl-1H-indol-1-yl)acetic Acid Ethyl Ester To chlorosulfonic acid (1.5 mL) at 0° C. under nitrogen was added portionwise over 10 minutes 2-(3-benzyl-5-fluoro-2-methyl-1H-indol-1-yl)acetic acid ethyl ester (900 mg, 2.76 mmol). After stirring at this temperature for 2 hours the solution was warmed to room temperature and stirred for a further 2 hours. The reaction mixture was then poured onto ice, and extracted with ethyl acetate. The separated organics were dried over anhydrous magnesium sulfate, filtered and evaporated in vacuo to give 2-(3-(4-(chlorosulfonyl)benzyl)-5-fluoro-2-methyl-1H-indol-1-yl)acetic acid ethyl ester (~1.1 g, 2.59 mmol, 94%) as a brown oil, which was used directly without further purification.

$^1$H NMR (d$_6$ DMSO): 7.46 (2H, d, J 8.0 Hz), 7.35 (1H, dd, J 8.9 & 4.3), 7.15-7.09 (3H, m), 6.86 (1H, td, J 9.3 & 2.5 Hz), 5.07 (2H, s), 4.14 (2H, obs. q, J 7.1 Hz), 4.00 (2H, obs. s), 2.30 (3H, s), 1.20 (3H, t, J 7.1 Hz).

Using 2-(3-(4-(chlorosulfonyl)benzyl)-5-fluoro-2-methyl-1H-indol-1-yl)acetic acid ethyl ester as a starting material, Compound 10 was then prepared in a similar manner to Compound 2, following Procedures Q & L.

LCMS RT=7.52 min (12.5 min run time), MH$^+$ 445.3

$^1$H NMR (d$_6$ DMSO): 7.61 (2H, d, J 8.4 Hz), 7.46 (2H, d, J 8.4 Hz), 7.36 (1H, dd, J 8.9 & 4.4 Hz), 7.12 (1H, dd, J 9.9 & 2.5 Hz), 6.87 (1H, td, J 9.3 & 2.5 Hz), 4.95 (2H, s), 4.13 (2H, s), 2.85-2.82 (4H, m), 2.33 (3H, s), 1.51-1.47 (4H, m), 1.36-1.33 (2H, m).

EXAMPLE 2

Measurement of CRTH2 Antagonist Activity

Materials and Methods

Materials

Mono-poly resolving medium was obtained from Dainippon Pharmaceuticals (Osaka, Japan). Macs anti-CD16 microbeads were from Miltenyi biotec (Bisley, Surrey). ChemoTx plates were purchased from Neuroprobe (Gaithersburg, Md.). Poly-D-lysine coated 96-well plates were obtained from Greiner (Gloucestershire, UK). [$^3$H]PGD$_2$ was from Amersham Biosciences (Buckinghamshire, UK). [$^3$H]SQ29548 was purchased from Perkin Elmer Life Sciences (Buckinghamshire, UK). All other reagents were obtained from Sigma-Aldrich (Dorset, UK), unless otherwise stated.

Methods

Cell Culture

Chinese Hamster Ovary cells were transfected with CRTH2 or DP receptors (CHO/CRTH2 and CHO/DP) and were maintained in culture in a humidified atmosphere at 37° C. (5% CO$_2$) in Minimum Essential Medium (MEM) supplemented with 10% foetal bovine serum, 2 mM glutamine, and 1 mg ml$^{-1}$ active G418. The cells were passaged every 2-3 days. For radioligand binding assay, cells were prepared in triple-layer flasks or in 175 cm$^2$ square flasks (for membrane preparation.

Preparation of Cell Membranes

Membranes were prepared either from CHO/CRTH2 and CHO/DP cells, or from platelets (as a source of TP receptors). CHO cells grown to confluency were washed with PBS and detached using a Versene solution (15 ml per flask). When the cells were grown in 175 cm$^2$ square flask, they were collected by scrapping in PBS. The cell suspensions were centrifuged (1,700 rpm, 10 min, 4° C.) and resuspended in 15 ml of buffer (1×HBSS, supplemented with 10 mM HEPES, pH 7.3). Cell suspensions were then homogenised using an Ultra Turrax at setting 4-6 for 20 s. The homogenate was centrifuged at 1,700 rpm for 10 min and the supernatant was collected and centrifuged at 20,000 rpm for 1 h at 4° C. The resulting pellet was resuspended in buffer and stored at −80° C. in aliquots of 200-500 μl. The protein concentration was determined by the method of Bradford (1976), using bovine serum albumin as standard. The platelets were washed by centrifugation at 600×g for 10 min and resuspended in ice-cold assay buffer (10 mM Tris-HCl, pH 7.4, 5 mM Glucose, 120 mM NaCl, 10

μM indomethacin) and directly centrifuged at 20,000 rpm for 30 min at 4° C. The resulting pellet was treated as described above.

Radioligand Binding Assays

[$^3$H]PGD$_2$ (160 Ci/mmol) binding experiments were performed on membranes prepared as described above. Assays were performed in a final volume of 100 μl of buffer (1×HBSS/HEPES 10 mM, pH 7.3). Cell membranes (15 μg) were preincubated at room temperature with varying concentration of competing ligand for 15 min. [$^3$H]PGD$_2$ was then added and the incubation continued for a further one hour at room temperature. The reaction was terminated by the addition of 200 μl ice-cold assay buffer to each well, followed by rapid filtration through Whatman GF/B glass fibre filters using a Unifilter Cell harvester (PerkinElmer Life Sciences) and six washes of 300 μl of ice-cold buffer. The Unifilter plates were dried at room temperature for at least 1 h and the radioactivity retained on the filters was determined on a Beta Trilux counter (PerkinElmer Life Sciences), following addition of 40 μl of Optiphase Hi-Safe 3 (Wallac) liquid scintillation. Non specific binding was defined in the presence of 10 μM unlabelled PGD$_2$. Assays were performed in duplicate.

The results of the radioligand binding experiments to the CRTH2 are shown in Table 1.

TABLE 1

Radioligand binding data ($K_i$ on CRTH2 Receptor).

| Compound | $K_i$ (nM) |
|---|---|
| 1 | 0.02 |
| 2 | 0.04 |
| 3 | 0.2 |
| 4 | 55 |
| 6 | 2 |
| 7 | 5 |
| 8 | 3 |
| 9 | 100 |
| 10 | 1 |

EXAMPLE 3

Human Whole Blood Eosinophil Shape Change Assay

Compounds 1 to 9 were assayed for their effect on PGD$_2$ induced eosinophil shape change.

Methods

Shape Change Assay in Whole Blood

Compounds (1 μl, 200× final concentration) were added directly to 200 μl whole blood, mixed well and incubated for 15 min, 37° C., 5% CO$_2$. After this time, cell shape was fixed by addition of 300 μl Cytofix™ buffer (BD Biosciences), 15 min on ice. 10 ml RBC lysis buffer was added to the fixed cells, incubated 5 min, at room temperature and centrifuged, 300×g for 5 min. Supernatant (containing lysed red cells) was removed and the lysis step was repeated. Leukocytes were resuspended in 250 μl RPMI/10% FCS and shape change analysed by FACS. Eosinophils were gated out based on their autofluorescence and 2000 eosinophil events were counted per sample. Data were analysed in triplicate.

The results for the eosinophil shape change assay are shown in Table 2.

TABLE 2

IC$_{50}$ Values for the Effect of Test Compounds on 10 nM PGD$_2$-induced Eosinophil Shape Change

| Compound | Value (nM) |
|---|---|
| 1 | 6 |
| 2 | 5 |
| 3 | 7 |
| 5 | 5 |
| 6 | 85 |
| 7 | 44 |
| 8 | 240 |

Tables 1 and 2 show that the compounds of the invention, and in particular Compounds 1, 2, 3 and 5 not only have high intrinsic activity but that this activity is maintained in whole blood.

The invention claimed is:

1. A compound of general formula (I)

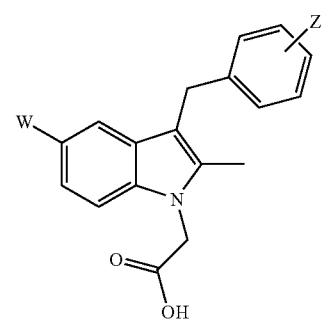

(I)

wherein
W is chloro or fluoro;
Z is a group SO$_2$R$^1$;
wherein R$^1$ is —C$_3$-C$_8$ cycloalkyl or heterocyclyl either of which is optionally substituted with one or more substituents chosen from halo, —CN, —C$_1$-C$_6$ alkyl, —SOR$^3$, —SO$_2$R$^3$, —SO$_2$N(R$^2$)$_2$, —N(R$^2$)$_2$, —NR$^2$C(O)R$^3$, —CO$_2$R$^2$, —CONR$^2$R$^3$, —NO$_2$, —OR$^2$, —SR$^2$, —O(CH$_2$)$_p$OR$^2$, or —O(CH$_2$)$_p$O(CH$_2$)$_q$OR$^2$ wherein each R$^2$ is independently hydrogen, —C$_1$-C$_6$ alkyl, —C$_3$-C$_8$ cycloalkyl, aryl or heteroaryl;
each R$^3$ is independently, —C$_1$-C$_6$ alkyl, —C$_3$-C$_8$ cycloalkyl, aryl or heteroaryl; and
p and q are each independently an integer from 1 to 3;
or a pharmaceutically acceptable salt thereof.

2. A compound of general formula (II):

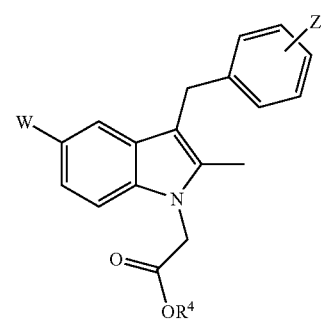

II wherein

W is chloro or fluoro;

Z is a group $SO_2R^1$;

wherein $R^1$ is $—C_3-C_8$ cycloalkyl or heterocyclyl either of which is optionally substituted with one or more substituents chosen from halo, —CN, —$C_1-C_6$ alkyl, —$SOR^3$, —$SO_2R^3$, —$SO_2N(R^2)_2$, —$N(R^2)_2$, —$NR^2C(O)R^3$, —$CO_2R^2$, —$CONR^2R^3$, —$NO_2$, —$OR^2$, —$SR^2$, —$O(CH_2)_pOR^2$, or —$O(CH_2)_pO(CH_2)_qOR^2$ wherein each $R^2$ is independently hydrogen, —$C_1-C_6$ alkyl, —$C_3-C_8$ cycloalkyl, aryl or heteroaryl;

each $R^3$ is independently, —$C_1-C_6$ alkyl, —$C_3-C_8$ cycloalkyl, aryl or heteroaryl;

p and q are each independently an integer from 1 to 3;

$R^4$ is $C_1-C_6$ alkyl, $C_1-C_6$ alkyl substituted with aryl, aryl, $(CH_2)_mOC(=O)C_1-C_6$alkyl, $((CH_2)_mO)_nCH_2CH_2X$, $(CH_2)_mN(R^5)_2$ or $CH((CH_2)_mO(C=O)R^6)_2$;

m is 1 or 2;

n is 1-4;

X is $OR^5$ or $N(R^5)_2$;

$R^5$ is hydrogen or methyl; and $R^6$ is $C_1-C_{18}$ alkyl;

or a pharmaceutically acceptable salt thereof.

3. A compound as claimed in claim 1 or claim 2, wherein W is fluoro.

4. A compound as claimed in claim 1 or claim 2, wherein the group $R^1$ is a substituted or unsubstituted pyrrole, piperidine, cyclobutyl, cyclopentyl or cyclohexyl group.

5. A compound as claimed in claim 4 wherein $R^1$ is a cyclopentyl, cyclohexyl, pyrrolidinyl or piperidinyl group.

6. A compound as claimed in claim 1 or claim 2, wherein the group Z is at the 2-position of the phenyl ring to which it is attached.

7. A compound selected from the group consisting of:
2-(3-(2-(cyclohexylsulfonyl)benzyl)-5-fluoro-2-methyl-1H-indol-1-yl)acetic acid;
2-(5-fluoro-2-methyl-3-(2-methyl-3-(2-(piperidin-1-ylsulfonyl)benzyl)-1H-indol-1-yl)acetic acid;
2-(3-(2-(cyclopentylsulfonyl)benzyl)-5-fluoro-2-methyl-1H-indol-1-yl)acetic acid;
2-(5-fluoro-2-methyl-3-(3-(piperidin-1-ylsulfonyl)benzyl)-1H-indol-1-yl)acetic acid;
2-(5-fluoro-2-methyl-3-(2-(pyrrolidin-1-ylsulfonyl)benzyl)-1H-indol-1-yl)acetic acid;
2-(3-(4-(cyclohexylsulfonyl)benzyl)-5-fluoro-2-methyl-1H-indol-1-yl)acetic acid;
2-(3-(4-(cyclopentylsulfonyl)benzyl)-5-fluoro-2-methyl-1H-indol-1-yl)acetic acid;
2-(3-(2-(cyclobutylsulfonyl)benzyl)-5-fluoro-2-methyl-1H-indol-1-yl)acetic acid;
2-(5-fluoro-2-methyl-3-(3-(pyrrolidin-1-ylsulfonyl)benzyl)-1H-indol-1-yl)acetic acid;
2-(5-fluoro-2-methyl-3-(4-(piperidin-1-ylsulfonyl)benzyl)-1H-indol-1-yl)acetic acid;
and the $C_1-C_6$ alkyl, aryl, $(CH_2)_mOC(=O)C_1-C_6$alkyl, $((CH_2)_mO)_nCH_2CH_2X$, $(CH_2)_mN(R^5)_2$ or $CH((CH_2)_mO(C=O)R^6)_2$ esters thereof; wherein m is 1 or 2;

n is 1-4;

X is $OR^5$ or $N(R^5)_2$;

$R^5$ is hydrogen or methyl; and $R^6$ is $C_1-C_{18}$ alkyl or a pharmaceutically acceptable salt thereof.

8. A process for the preparation of a compound of general formula (I) as claimed in claim 1, the process comprising reacting with a base, a compound of general formula (II)

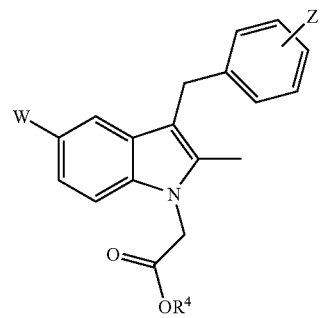

wherein

W and Z are defined in claim 1; and $R^4$ is $C_1-C_6$ alkyl.

9. A method for the treatment of a disease or condition selected from allergic asthma, perennial allergic rhinitis, seasonal allergic rhinitis, atopic dermatitis, contact hypersensitivity, conjunctivitis, allergic conjunctivitis, vernal keratoconjunctivitis or atopic keratoconjunctivitis, the method comprising administering to a patient in need of such treatment a suitable amount of a compound as claimed in any one of claims 1 and 2.

10. A method as claimed in claim 9 further comprising administering one or more additional active agents selected from the group consisting of:

other CRTH2 antagonists, Suplatast tosylate, β2 adrenoreceptor agonists, methylxanthines, mast cell stabilisers, muscarinic receptor antagonists, antihistamines, $\alpha_1$ and $\alpha_2$ adrenoreceptor agonists, modulators of chemokine receptor function, leukotriene antagonists, leukotriene biosynthesis inhibitors, 5-lipoxygenase activating protein inhibitors, N-(5-substituted)-thiophene-2-alkylsolfonamides, 2,6-di-tert-butylphenol hydrazones, methoxytetrahydropyrans, pyridinyl-substituted-2-cyanonaphthalene compounds, 2-cyanoquinoline compounds, indole and quinoline compounds, phosphodiesterase inhibitors, anti-IgE antibody therapies, anti-infectives, anti-fungals, immunosuppressants, immunotherapy agents, corticosteroids, drugs which promote Th1 cytokine response, other antagonists of $PGD_2$ acting at other receptors, drugs that modulate cytokine production, TNF receptor immunoglobulin molecules, inhibitors of other TNF isoforms, non-selective COX-1/COX-2 inhibitors, COX-2 inhibitors, low dose methotrexate, lefunomide, ciclesonide, hydroxychloroquine, d-penicillamine, auranofin, parenteral or oral gold, drugs that modulate the activity of Th2 cytokines IL-4 and IL-5, PPAR-γ agonists, anti-RSV antibodies or agents that may be used to treat rhinovirus infection.

11. A pharmaceutical composition comprising a compound as claimed in claim 1 or claim 2 together with a pharmaceutical excipient or carrier.

12. A composition as claimed in claim 11 formulated for oral, rectal, nasal, bronchial, topical, vaginal or parenteral administration.

13. A composition as claimed in claim 11, comprising one or more additional active agents selected from the group consisting of:

other CRTH2 antagonists, Suplatast tosylate, β2 adrenoreceptor agonists, methylxanthines, mast cell stabilisers, muscarinic receptor antagonists, antihistamines, $\alpha_1$ and $\alpha_2$ adrenoreceptor agonists, modulators of chemokine receptor function, leukotriene antagonists, leukotriene biosynthesis inhibitors, 5-lipoxygenase activating protein inhibitors, N-(5-substituted)-thiophene-2-alkylsolfonamides, 2,6-di-tert-butylphenol hydrazones, methoxytetrahydropyrans, pyridinyl-substituted-2-cyanonaphthalene compounds, 2-cyanoquinoline compounds, indole and quinoline compounds, phosphodiesterase inhibitors, anti-IgE antibody therapies, anti-infectives, anti-fungals, immunosuppressants, immunotherapy agents, corticosteroids, drugs which promote Th1 cytokine response, other antagonists of $PGD_2$ acting at other receptors, drugs that modulate cytokine production, TNF receptor immunoglobulin molecules, inhibitors of other TNF isoforms, non-selective COX-1/COX-2 inhibitors, COX-2 inhibitors, low dose methotrexate, lefunomide, ciclesonide, hydroxychloroquine, d-penicillamine, auranofin, parenteral or oral gold, drugs that modulate the activity of Th2 cytokines IL-4 and IL-5, PPAR-γ agonists, anti-RSV antibodies and agents that may be used to treat rhinovirus infection.

14. A process for the preparation of a pharmaceutical composition comprising bringing a compound of claim 1 or claim 2 in conjunction or association with a pharmaceutically or veterinarily acceptable carrier or vehicle.

15. A kit comprising
(a) a first container comprising a compound of claim 1 or claim 2
and
(b) a second container comprising an additional agent useful for the treatment of diseases and conditions
selected from the group consisting of asthma, allergic asthma, bronchial asthma, exacerbations of asthma and related allergic diseases caused by viral infection, exacerbations caused by rhinovirus and respiratory syncytial virus intrinsic, extrinsic, exercise-induced, drug-induced and dust-induced asthma, treatment of cough, chronic cough associated with inflammatory and secretory conditions of the airways and iatrogenic cough, acute and chronic rhinitis, rhinitis medicamentosa, vasomotor rhinitis, perennial allergic rhinitis, seasonal allergic rhinitis, nasal polyposis, acute viral infection, common cold, infection due to respiratory syncytial virus, influenza, coronavirus and adenovirus, atopic dermatitis, contact hypersensitivity, eczematous dermatitis, phyto dermatitis, photo dermatitis, sebhorroeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa urticaria, angioedema, vasculitides, toxic erythemas, cutaneous eosinophilias, alopecia areata, male-pattern baldness, Sweet's syndrome, Weber-Christian syndrome, erythema multiforme, cellulitis, panniculitis, cutaneous lymphomas, non-melanoma skin cancer and other dysplastic lesions; blepharitis conjunctivitis, allergic conjunctivitis, anterior and posterior uveitis, choroiditis, autoimmune, degenerative or inflammatory disorders affecting the retina, ophthalmitis; bronchitis, infectious and eosinophilic bronchitis, emphysema, bronchiectasis, farmer's lung, hypersensitivity pneumonitis, idiopathic interstitial pneumonias, complications of lung transplantation, vasculitic and thrombotic disorders of the lung vasculature, pulmonary hypertension, food allergies, gingivitis, glossitis, periodontits, oesophagitis, reflux, and eosinophilic gastroenteritis, proctitis, pruris ani, celiac disease, food-related allergies, inflammatory bowel disease, ulcerative colitis and Crohn's disease, mastocytosis and also other CRTH2-mediated diseases, autoimmune diseases such as hyper IgE syndrome, Hashimoto's thyroiditis, Graves' disease, Addison's disease, idiopathic thrombocytopaenic purpura, eosinophilic paschiitis, antiphospholipid syndrome and systemic lupus erythematosus, AIDS, leprosy, Sezary syndrome, paraneoplastic syndrome, mixed and undifferentiated connective tissue diseases, inflammatory myopathies, dermatomyositis and polymyositis, polymalgia rheumatica, juvenile arthritis, rheumatic fever, vasculitides, giant cell arteritis, Takayasu's arteritis, Churg-Strauss syndrome, polyarteritis nodosa, microscopic polyarteritis, temporal arteritis, myasthenia gravis, acute and chronic pain, neuropathic pain syndromes, central and peripheral nervous system complications of malignant, infectious or autoimmune processes, low back pain, familial Mediterranean Fever, Muckle-Wells syndrome, Familial Hibernian fever, Kikuchi disease, psoriasis, acne, multiple sclerosis, allograft rejection, reperfusion injury, chronic obstructive pulmonary disease, as well as rheumatoid arthritis, Still's disease, ankylosing spondylitis, reactive arthritis, undifferentiated spondarthropathy, psoriatic arthritis, septic arthritis and other infection-related arthopathies and bone disorders and osteoarthritis; acute and chronic crystal-induced synovitis, urate gout, calcium pyrophosphate deposition disease, calcium paptite related tendon syndrome and synovial inflammation, Behcet's disease, primary and secondary Sjogren's syndrome systemic sclerosis and limited scleroderma; hepatitis, cirrhosis of the liver, cholecystitis, pancreatitis, nephritis, nephritic syndrome, cystitis and Hunner's ulcer, acute and chronic urethritis, prostatitis, epididymitis, oophoritis, salpingitis, vulvo-vaginitis, Peyronie's disease, erectile dysfunction, Alzheimer's disease, other dementing disorders; pericarditis, myocarditis, inflammatory and autoimmune cardiomyopathies, myocardial sarcoid, ischaemic reperfusion injuries, endocarditis, valvulitis, aortitis, phlebitis, thrombosis, treatment of common cancers and fibrotic conditions such as idiopathic pulmonary fibrosis, cryptogenic fibrosing alveolitis, keloids, excessive fibrotic scarring/adhesions post surgery, liver fibrosis, liver fibrosis associated with hepatitis B and C, uterine fibroids, sarcoidosis, neurosarcoidosis, scleroderma, kidney fibrosis resulting from diabetes, fibrosis associated with RA, atherosclerosis, cerebral atherosclerosis, vasculitis, myocardial fibrosis resulting from myocardial infarction, cystic fibrosis, restenosis, systemic sclerosis, Dupuytren's disease, fibrosis complicating anti-neoplastic therapy and chronic infection, tuberculosis, aspergillosis and other fungal infections, CNS fibrosis following stroke and the promotion of healing without fibrotic scarring.

16. The kit as claimed in claim 15 wherein said additional agent is selected from the group consisting of:
other CRTH2 antagonists, Suplatast tosylate, β2 adrenoreceptor agonists, methylxanthines, mast cell stabilisers, muscarinic receptor antagonists, antihistamines, $\alpha_1$ and $\alpha_2$ adrenoreceptor agonists, modulators of chemokine receptor function, leukotriene antagonists, leukotriene biosynthesis inhibitors, 5-lipoxygenase activating protein inhibitors, N-(5-substituted)-thiophene-2-alkylsolfonamides, 2,6-di-tert-butylphenol hydrazones, methoxytetrahydropyrans, pyridinyl-substituted-2-cyanonaphthalene compounds, 2-cyanoquinoline compounds, indole and quinoline compounds, phosphodiesterase inhibitors, anti-IgE antibody therapies, anti-infectives, anti-fungals, immunosuppressants, immunotherapy agents, corticosteroids, drugs which promote Th1 cytokine response, other antagonists of $PGD_2$ acting at other receptors, drugs that modulate cytokine production, TNF receptor immunoglobulin molecules, inhibitors of other TNF isoforms, non-selective COX-1/COX-2 inhibitors, COX-2 inhibitors, low dose methotrexate, lefunomide, ciclesonide, hydroxychloroquine, d-penicillamine, auranofin, parenteral or oral gold, drugs that modulate the activity of Th2 cytokines IL-4 and IL-5, PPAR-γ agonists, anti-RSV antibodies and agents that may be used to treat rhinovirus infection.

17. A pharmaceutical composition as claimed in claim 13 wherein the additional active agent is a leukotriene antagonist.

18. A pharmaceutical composition as claimed in claim 17 wherein the leukotriene antagonist is montelukast.

19. A kit as claimed in claim 16 wherein the additional active agent is a leukotriene antagonist.

20. A kit as claimed in claim 19 wherein the leukotriene antagonist is montelukast.

21. A compound according to claim 7 selected from the group consisting of:
- 2-(3-(2-(cyclohexylsulfonyl)benzyl)-5-fluoro-2-methyl-1H-indol-1-yl)acetic acid;
- 2-(5-fluoro-2-methyl-3-(2-(piperidin-1-ylsulfonyl)benzyl)-1H-indol-1-yl)acetic acid;
- 2-(3-(2-(cyclopentylsulfonyl)benzyl)-5-fluoro-2-methyl-1H-indol-1-yl)acetic acid;
- 2-(5-fluoro-2-methyl-3-(3-(piperidin-1-ylsulfonyl)benzyl)-1H-indol-1-yl)acetic acid;
- 2-(5-fluoro-2-methyl-3-(2-(pyrrolidin-1-ylsulfonyl)benzyl)-1H-indol-1-yl)acetic acid;
- 2-(3-(4-(cyclohexylsulfonyl)benzyl)-5-fluoro-2-methyl-1H-indol-1-yl)acetic acid;
- 2-(3-(4-(cyclopentylsulfonyl)benzyl)-5-fluoro-2-methyl-1H-indol-1-yl)acetic acid;
- 2-(3-(2-(cyclobutylsulfonyl)benzyl)-5-fluoro-2-methyl-1H-indol-1-yl)acetic acid;
- 2-(5-fluoro-2-methyl-3-(3-(pyrrolidin-1-ylsulfonyl)benzyl)-1H-indol-1-yl)acetic acid;
- 2-(5-fluoro-2-methyl-3-(4-(piperidin-1-ylsulfonyl)benzyl)-1H-indol-1-yl)acetic acid;

and the pharmaceutically acceptable salts thereof.

22. A kit according to claim 15, wherein the additional active agent is useful for the treatment of diseases or conditions selected from the group consisting of allergic asthma, perennial allergic rhinitis, seasonal allergic rhinitis, atopic dermatitis, contact hypersensitivity, conjunctivitis, eosinophilic bronchitis, food allergies, eosinophilic gastroenteritis, inflammatory bowel disease, ulcerative colitis, Crohn's disease, mastocytosis, autoimmune disease, psoriasis, acne, multiple sclerosis, allograft rejection, reperfusion injury, chronic obstructive pulmonary disease, rheumatoid arthritis, psoriatic arthritis, osteoarthritis, fibrotic diseases caused/exacerbated by Th2 immune responses, idiopathic pulmonary fibrosis and hypertrophic scars.

\* \* \* \* \*